US008404817B2

(12) United States Patent
Sherman et al.

(10) Patent No.: US 8,404,817 B2
(45) Date of Patent: Mar. 26, 2013

(54) HUMANIZED ANTI-PROSTATE STEM CELL ANTIGEN MONOCLONAL ANTIBODY

(75) Inventors: Mark A. Sherman, Pasadena, CA (US); Anna M. Wu, Sherman Oaks, CA (US); Robert E. Reiter, Los Angeles, CA (US)

(73) Assignees: City of Hope, Duarte, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/308,783

(22) Filed: Dec. 1, 2011

(65) Prior Publication Data

US 2012/0077962 A1  Mar. 29, 2012

Related U.S. Application Data

(62) Division of application No. 11/432,304, filed on May 10, 2006, now Pat. No. 8,088,908.

(60) Provisional application No. 60/679,848, filed on May 10, 2005.

(51) Int. Cl.
*C12P 21/08* (2006.01)
(52) U.S. Cl. ............... 530/387.3; 530/391.1; 530/391.3; 530/391.7
(58) Field of Classification Search .................... None
See application file for complete search history.

(56) References Cited

U.S. PATENT DOCUMENTS

| | | |
|---|---|---|
| 5,859,205 A | 1/1999 | Adair et al. |
| 6,258,939 B1 | 7/2001 | Reiter et al. |
| 6,261,789 B1 | 7/2001 | Reiter et al. |
| 6,261,791 B1 | 7/2001 | Reiter et al. |
| 6,267,960 B1 | 7/2001 | Reiter et al. |
| 6,541,212 B2 | 4/2003 | Reiter et al. |
| 6,541,224 B2 | 4/2003 | Yu et al. |
| 6,544,761 B2 | 4/2003 | Greene et al. |
| 6,639,055 B1 | 10/2003 | Carter et al. |
| 6,756,036 B2 | 6/2004 | Reiter et al. |
| 6,790,939 B2 | 9/2004 | Reiter et al. |
| 6,801,098 B2 | 10/2004 | Reiter et al. |
| 6,818,216 B2 | 11/2004 | Young et al. |
| 6,825,326 B2 | 11/2004 | Reiter et al. |
| 6,875,433 B2 | 4/2005 | Hart et al. |
| 6,881,822 B2 | 4/2005 | Reiter et al. |
| 6,960,443 B2 | 11/2005 | Reiter et al. |
| 6,979,730 B2 | 12/2005 | Reiter et al. |
| 7,407,656 B2 | 8/2008 | Reiter et al. |
| 7,417,113 B2 | 8/2008 | Reiter et al. |
| 7,485,296 B2 | 2/2009 | Reiter et al. |
| 7,527,786 B2 | 5/2009 | Reiter et al. |
| 7,985,840 B2 | 7/2011 | Fuh et al. |
| 2002/0119157 A1 | 8/2002 | Reiter et al. |
| 2002/0136689 A1 | 9/2002 | Reiter et al. |
| 2003/0153016 A1 | 8/2003 | Reiter et al. |
| 2005/0026229 A1 | 2/2005 | Reiter et al. |
| 2005/0059099 A1 | 3/2005 | Reiter et al. |
| 2006/0147451 A1 | 7/2006 | Kirchhofer et al. |

FOREIGN PATENT DOCUMENTS

WO   WO 2005/086875 A2   9/2005

OTHER PUBLICATIONS

[Fundamental Immunology p. 242 (William E. Paul, M.D. ed., 3d ed; 1993].*
Adams, G.P. and Weiner, L.M. 2005. Monoclonal antibody therapy of cancer. Nat Biotechnol 23:1147-1157.
Antibody Engineering Ed. Borrecaeck, 2nd Ed., pp. 179-180 (1995).
Bebbington, C., et al. 1992. High-level expression of a recombinant antibody from myeloma cells using a glutamine synthetase gene as an amplifiable selection marker. Biotechnology 10:169-175.
Berman, H.M., et al. 2002. The Protein Data Bank. Acta Crystallogr D Biol Crystallogr 58:899-907.
Boehm, M.K., et al. 2000. Crystal structure of the anti-(carcinoembryonic antigen) single-chain Fv antibody MFE-23 and a model for antigen binding based on intermolecular contacts. Biochem J 346 Pt 2:519-528.
Brechbiel, M.W., Gansow, O.A. 1991. Backbone-substituted DTPA ligands for 90Y radioimmunotherapy. Bioconjug Chem 2:187-194.
Bruggemann, M., et al. 1991. Human antibody production in transgenic mice: expression from 100 kb of the human IgH locus. Eur J Immunol 21:1323-1326.
Carter, P., et al., "Humanization of an Anti-p185$^{HER2}$ Antibody for Human Cancer Therapy," PNAS 89:4285-4289 (1992).
Chow, P.L., Rannou, F.R., Chatziioannou, A.F. 2005. Attenuation correction for small animal PET tomographs. Phys Med Biol 50:1837-1850.
Cobleigh, M.A., et al. 1999. Multinational study of the efficacy and safety of humanized anti-HER2 monoclonal antibody in women who have HER2-overexpressing metastatic breast cancer that has progressed after chemotherapy for metastatic disease. J Clin Oncol 17:2639-2648.
Coloma, M.J., et al. 1992. Novel vectors for the expression of antibody molecules using variable regions generated by polymerase chain reaction. J Immunol Methods 152:89-104.
Craft, N., et al. 1999. Evidence for clonal outgrowth of androgen-independent prostate cancer cells from androgen-dependent tumors through a two-step process. Cancer Res 59:5030-5036.
Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier," Virology 202:540-549 (1994).
Defrise, M., et al. 1997. Exact and approximate rebinning algorithms for 3-D PET data. IEEE Trans Med Imaging 16:145-158.

(Continued)

*Primary Examiner* — Brad Duffy
(74) *Attorney, Agent, or Firm* — Perkins Coie LLP; Patrick D. Morris

(57) ABSTRACT

Prostate stem cell antigen (PSCA) is expressed in the majority of prostate cancer patients, making it an ideal target for cancer immunotherapy. Murine monoclonal antibody 1G8 binds to PSCA with nanomolar affinity, but its efficacy as a therapeutic agent is limited by the generation of a HAMA response. The present invention discloses humanized 1G8 antibodies in which the majority of the mouse-derived epitopes have been removed. These humanized antibodies bind PSCA with high affinity and specificity, and have been shown to reduce human bladder tumor take in a nude mouse model. These characteristics make the humanized antibodies of the present invention attractive agents for the treatment and detection of tumors expressing PSCA.

4 Claims, 7 Drawing Sheets

OTHER PUBLICATIONS

Desjarlais, J. R., et al., "Optimizing Engagement of the Immune System by Anti-Tumor Antibodies: An Engineer's Perspective," Drug Discov. Today 12(21/22):898-910 (2007).
Eigenbrot, C., et al. 1993. X-ray structures of the antigen-binding domains from three variants of humanized anti-p185HER2 antibody 4D5 and comparison with molecular modeling. J Mol Biol 229:969-995.
Ewert, S., et al. 2003. Biophysical properties of human antibody variable domains. J Mol Biol 325:531-553.
Foote, J., Winter, G. 1992. Antibody framework residues affecting the conformation of the hypervariable loops. J Mol Biol 224:487-499.
Geissler, F., et al. 1992. Intracellular catabolism of radiolabeled anti-mu antibodies by malignant B-cells. Cancer Res 52:2907-2915.
George, J., et al., "Differential Effects of Anti-$\beta_2$-Glycoprotein I Antibodies on Endothelial Cells and on the Manifestations of Experimental Antiphospholipid Syndrome," Circulation 97:900-906 (1998).
Greenspan, N. S., et al., "Defining Epitopes: It's Not as Easy as it Seems," Nat. Biotech. 7:936-937 (1999).
Gu, Z., et al. 2000. Prostate stem cell antigen (PSCA) expression increases with high gleason score, advanced stage and bone metastasis in prostate cancer. Oncogene 19:1288-1296.
Gu, Z., et al. 2005. Anti-prostate stem cell antigen monoclonal antibody 1G8 induces cell death in vitro and inhibits tumor growth in vivo via a Fc-independent mechanism. Cancer Res 65:9495-9500.
Gussow, D., et al., "Humanization of Monoclonal Antibodies," Methods in Enzymology 203:99-121 (1991).
Horton, R.M., et al. 1989. Engineering hybrid genes without the use of restriction enzymes: gene splicing by overlap extension. Gene 77:61-68.
Hostetier, K. A., et al., "Immunochemical Evidence for Multiple Steroid-Inducible Hepatic Cytochromes P-450 in the Rat," Biochem. J. 245:27-33 (1987).
Jalkut, M. W., et al., "Role of Prostate Stem Cell Antigen in Prostate Cancer Research," Curr. Opin. Urol. 12:401-406 (2002).
Jones, P.T., et al. 1986. Replacing the complementarity-determining regions in a human antibody with those from a mouse. Nature 321:522-525.
Kenanova, V., et al. 2005. Tailoring the pharmacokinetics and positron emission tomography imaging properties of anti-carcinoembryonic antigen single-chain Fv-Fc antibody fragments. Cancer Res 65:622-631.
Kinahan, P.E., Rogers, J.G. 1989. Analytic 3D image reconstruction using all detected events. IEEE Trans NS 36:964-968.
Kipriyanov, S. M., et al., "Generation and Production of Engineered Antibodies," Mol. Bio. 26:39-60 (2004).
Loening, A.M., Gambhir, S.S. 2003. AMIDE: a free software tool for multimodality medical image analysis. Mol Imaging 2:131-137.
Low, N.M., Holliger, P.H., Winter, G. 1996. Mimicking somatic hypermutation: affinity maturation. J Mol Biol 260:359-368.
Mariuzza, R. A., et al., "The Structural Basis of Antigen-Antibody Recognition," Annu. Rev. Biophys. Biophys. Chem. 16:139-159 (1987).
Maynard J., Georgiou, G. 2000. Antibody engineering. Annu Rev Biomed Eng 2:339-376.
Mendez, M.J., et al. 1997. Functional transplant of megabase human immunoglobulin loci recapitulates human antibody response in mice. Nat Genet 2:146-156.
Nanus, D.M., et al. 2003. Clinical use of monoclonal antibody HuJ591 therapy: targeting prostate specific membrane antigen. J Urol 170:S84-S88; discussion S8-S9.
O'Brien, S., Jones, T. 2003. Humanization of monoclonal antibodies by CDR grafting. Methods Mol Biol 207:81-100.
O'Connor, S.J., Meng, Y.G., Rezaie, A.R., Presta, L.G. 1998. Humanization of an antibody against human protein C and calcium-dependence involving framework residues. Protein Eng 11:321-328.
Olafsen, T., et al. 2004. Characterization of engineered anti-p185HER-2 (scFv-CH3)2 antibody fragments (minibodies) for tumor targeting. Protein Eng Des Sel 17:315-323.
Olafsen, T., et al. 2005. Optimizing radiolabeled engineered anti-p185HER2 antibody fragments for in vivo imaging. Cancer Res 65:5907-5916.
Paemen, L., et al., "Monoclonal Antibodies Specific for Natural Human Neutrophil Gelatinase B Used for Affinity Purification, Quantitation by Two-Site ELISA and Inhibition of Enzymatic Activity," Ur. J. Biochem. 234:759-765 (1995).
Pearson, W.R., Lipman, D.J. 1988. Improved tools for biological sequence comparison. Proc Natl Acad Sci USA 85:2444-2448.
Reiter, R.E., et al. 1998. Prostate stem cell antigen: a cell surface marker overexpressed in prostate cancer. Proc Natl Acad Sci USA 95:1735-1740.
Reiter, R.E., et al. 2000. Coamplification of prostate stem cell antigen (PSCA) and MYC in locally advanced prostate cancer. Genes Chromosomes Cancer 27:95-103.
Roguska, M. A., et al., "A Comparison of Two Murine Monoclonal Antibodies Humanized by CDR-Grafting and Variable Domain Resurfacing," Pro. Engin. 9(10):895-904 (1996).
Saffran, D.C., et al. 2001. Anti-PSCA mAbs inhibit tumor growth and metastasis formation and prolong the survival of mice bearing human prostate cancer xenografts. Proc Natl Acad Sci USA 98:2658-2663.
Schroff, R.W., Foon, K.A., Beatty, S.M., Oldham, R.K., and Morgan, A.C. Jr. 1985. Human anti-murine responses in patients receiving monoclonal antibody therapy. Cancer Res 45:879-885.
Shawler, D.L., Bartholomew, R.M., Smith, L.M., and Dillman, R.O. 1985. Human immune responses to multiple injections of murine monoclonal immunoglobulins. J Immunol 135:1530-1535.
Smith-Jones, P.M. 2004. Radioimmunotherapy of prostate cancer. Q J Nucl Med Mol Imaging 48:297-304.
Sundaresan, G., et al. 2003. 124I-labeled engineered anti-CEA minibodies and diabodies allow high-contrast, antigen-specific small-animal PET imaging of xenografts in athymic mice. J Nucl Med 44:1962-1969.
Uracz, W., et al., "Involvement of I-J Epitopes in the Self- and Allo-Recognition Sites of T Cells: Blocking of Syngeneic and Allogeneic Mixed Lymphocyte Reaction-Responder Cells by Monoclonal Anti-I-J Antibodies," PNAS 82:2905-2909 (1985).
Winter, G., Griffiths, A.D., Hawkins, R.E., Hoogenboom, H.R. 1994. Making antibodies by phage display technology. Annu Rev Immunol 12:433-455.
Worn, A., Pluckthun, A. 1999. Different equilibrium stability behavior of ScFv fragments: identification, classification, and improvement by protein engineering. Biochemistry 38:8739-8750.
Wu, A.M., et al. 2001. Multimerization of a chimeric anti-CD20 single-chain Fv-Fc fusion protein is mediated through variable domain exchange. Protein Eng 14:1025-1033.
Wu, A.M., Senter, P.D. 2005. Arming antibodies: prospects and challenges for immunoconjugates. Nat Biotechnol 23:1137-1146.
Wu, H., et al., "Humanization of a Murine Monoclonal Antibody by Simultaneous Optimization of Framework and CDR Residues," J. Mol. Biol. 294:151-162 (1999).
Xu, F.J., et al. 1997. Radioiodinated antibody targeting of the HER-2/neu oncoprotein. Nucl Med Biol 24:451-459.
Yazaki, P.J., et al. 2001a. Mammalian expression and hollow fiber bioreactor production of recombinant anti-CEA diabody and minibody for clinical applications. J Immunol Methods 253:195-208.
Yazaki, P.J., et al. 2001b. Tumor targeting of radiometal labeled anti-CEA recombinant T84.66 diabody and t84.66 minibody: comparison to radioiodinated fragments. Bioconjug Chem 12:220-228.
Yazaki, P.J., et al. 2004. Humanization of the anti-CEA T84.66 antibody based on crystal structure data. Protein Eng Des Sel 17:481-489.

* cited by examiner

Figure 1

V_L chain alignment (mismatch =20/106)

```
SEQ ID NO:1  1G8:  QVVLTQSPAIMSASPGEKVTMACSASSSVRFIHWYQQKSGTSPKRWIYDTSKLASGVPTRFSG
                   : ::::::::::::::::::::: :::::: :::::::::: :::: ::::::::: ::::
SEQ ID NO:3  1QOK: ENVLTQSPAIMSASPGEKVTITCSASSSVSYMHWFQQKPGTSPKLWIYSTSNLASGVPARFSG

SEQ ID NO:1  1G8:  SGSGTSYSLTISTMEAEDAATYCQQWSSSPFTFGSGTKLIIK
                   :::::::::::: ::::::::::::: :::: :::: :: :
SEQ ID NO:3  1QOK: SGSGTSYSLTISRMEAEDAATYCQQRSSYPLTFGAGTKLELK
```

V_H chain alignment (mismatch 22/112, excluding gap)

```
SEQ ID NO:2  1G8:  EVQLQQSGAELVRSGASVKLSCTASGFNIKDYYIHWVNQRPDQGLEWIGWIDPENGDTEFVPK
                   :: :::::::::::::::::::::::::::::::: ::: :::::::::::::::: ::::
SEQ ID NO:4  1QOK: QVKLQQSGAELVRSGTSVKLSCTASGFNIKDSYMHWLRQGPEQGLEWIGWIDPENGDTEYAPK

SEQ ID NO:2  1G8:  FQGKATMTADIFSNTAYLHLSSLTSEDTAVYYCKTG------GFWGQGTLVTVSA
                   ::::::: : : :::::::: ::::::::::::: :      ::::::::: :::
SEQ ID NO:4  1QOK: FQGKATFTTDTSSNTAYLQLSSLTSEDTAVYYCNEGTPTGPYYFDYWGQGTTVTVSS
```

| | | |
|---|---|---|
| SEQ ID NO:1 | muIG8: | QVVLTQSPAIMSASPGEKVTMACSASSSVR-FIHWYQQKSGTSPKRWIYDTSKLASGVPTRFSG |
| SEQ ID NO:5 | 4D5v8: | DIQMTQSPSSLSASVGDRVTITCRASQDVNTAVAWYQQKPGKAPKLLIYSASFLYSGVPSRFSG |
| SEQ ID NO:7 | huIG8-A/B: | DIQLTQSPSSLSASVGDRVTITCSASSSVR-FIHWYQQKPGKAPKRLIYDTSKLASGVPSRFSG |
|   |   | ─────────CDR-L1────────  ──────CDR-L2───── |

| | | |
|---|---|---|
| SEQ ID NO:1 | muIG8: | SGSGTSYSLTISTMEAEDAATYYCQQWSSSPFTFGSGTKLIIK |
| SEQ ID NO:5 | 4D5v8: | SRSGTDFTLTISSLQPEDFATYYCQQHYTTPPTFGQGTKVEIK |
| SEQ ID NO:7 | huIG8-A/B: | SGSGTDFTLTISSLQPEDFATYYCQQWSSSPFTFGQGTKVEIK |
|   |   | ────CDR-L3──── |

VH

| | | |
|---|---|---|
| SEQ ID NO:2 | muIG8: | EVQLQQSGAEIVRSGASVKLSCTASGFNIKDYYIHWVNQRPDQGLEWIGWIDPENGDTEFVPKFQG |
| SEQ ID NO:6 | 4D5v8: | EVQLVESGGGLVQPGGSLRLSCAASGFNIKDTYIHWVRQAPGKGLEWVARIYPTNGYTRYADSVKG |
| SEQ ID NO:8 | huIG8-A: | EVQLVESGGGLVQPGGSLRLSCAASGFNIKDYYIHWVRQAPGKGLEWVAWIDPENGDTEFADSVKG |
| SEQ ID NO:9 | huIG8-B: | EVQLVESGGGLVQPGGSLRLSCAASGFNIKDYYIHWVRQAPGKGLEWVAWIDPENGDTEFVPKFQG |
|   |   | ─CDR-H1── ────────CDR-H2──────── |

| | | |
|---|---|---|
| SEQ ID NO:2 | muIG8: | KATMTADIFSNTAYLHLSSLTSEDTAVYYCKTGG----------FWGQGTLVTVSA |
| SEQ ID NO:6 | 4D5v8: | RFTISADTSKNTAYLQMNSLRAEDTAVYYCSRWGGDGFYAMDYWGQGTLVTVSS |
| SEQ ID NO:8 | huIG8-A | RFTISADTSKNTAYLQMNSLRAEDTAVYYCKTGG----------FWGQGTLVTVSS |
| SEQ ID NO:9 | huIG8-B | RATISADTSKNTAYLQMNSLRAEDTAVYYCKTGG----------FWGQGTLVTVSS |
|   |   | ──CDR-H3── |

HUMANIZED ANTI-PROSTATE STEM CELL ANTIGEN MONOCLONAL ANTIBODY

CROSS-REFERENCE TO RELATED APPLICATION

The present application is a divisional application of U.S. application Ser. No. 11/432,304, filed May 10, 2006, now U.S. Pat. No. 8,088,908 which claims priority to U.S. Provisional Application No. 60/679,848, filed May 10, 2005, the disclosures of which are incorporated by reference herein in their entirety.

GOVERNMENT INTEREST

This invention was made with Government support of Grant number CA043904 awarded by the National Institutes of Health. The government has certain rights in this invention.

BACKGROUND

Prostate cancer is the most commonly diagnosed cancer in men, with approximately 1.7 million men in the U.S. having been diagnosed with this condition. Over 200,000 new cases of prostate cancer will be added per year and around 30,000 will die annually, making it the second leading cause of cancer-related deaths in men. The five-year survival rate with prostate cancer is 89%, with this percentage jumping to 100% for patients with localized tumors treated with conventional therapeutic approaches. However, once metastases or hormone-refractory disease develops, therapeutic options are limited. Hence, there is a need to develop new pharmaceuticals for the treatment of metastatic prostate cancer, as well as a need to identify new diagnostic markers that can better discriminate between indolent and aggressive variants of prostate cancer.

Antibody-based therapy using unconjugated, toxin-conjugated or radiolabeled reagents against tumor-associated target antigens has proven beneficial for solid and hematolymphoid neoplasms (Adams 2005; Wu 2005). There are currently 17 monoclonal antibodies (mAbs) approved by the FDA in the US. Of these, eight (five unconjugated and three conjugated) are approved for treatment of cancer (Adams 2005). One key issue with regard to the therapeutic use of monoclonal antibodies has been the response of the human immune system to xenogeneic antibodies. Clinical studies with murine monoclonal antibodies have shown effective tumor targeting, but have also resulted in rapid clearance of the murine antibody due to the generation of a human anti-murine antibody (HAMA) immune response (Schroff 1985; Shawler 1985). The present invention provides humanized antibodies for use in the diagnosis and treatment of prostate cancer with minimal HAMA response.

SUMMARY

In certain embodiments, a humanized antibody is provided that combines a human or humanized immunoglobulin framework with a binding site that recognizes the same epitope as murine monoclonal antibody 1G8. In certain embodiments, the humanized antibody may bind PSCA with a $K_A$ of at least about $2.5 \times 10^8$. In certain embodiments, the framework immunoglobulin may be a humanized antibody 4D5 version 8 in which one or more of the following residues have been replaced with equivalent residues from murine 1G8 monoclonal antibody (residues numbered according to Kabat system): L4, L24-L34, L46, L50-L56, L66, L70, L71, L89-L97, H26-H35, H48, H49, H50-H59, H60-H65, H66, H67, H69, and/or H93-H102. In these embodiments, the light chain variable region of the humanized antibody may have the amino acid sequence set forth in SEQ. ID. NO:7 or SEQ. ID. NO: 37 and the heavy chain variable region set forth in SEQ. ID. NO:8, SEQ. ID. NO:9, or SEQ. ID. NO:38. In certain embodiments, the humanized antibody may be associated with a conjugate such as a toxin, a cytokine, a chemotherapeutic agent, or a radiolabel.

In certain embodiments, an isolated polynucleotide is provided encoding a humanized antibody that combines a human or humanized immunoglobulin framework with a binding site that recognizes the same epitope as murine monoclonal antibody 1G8. In certain embodiments, the variable light chain of the humanized antibody may have the amino acid sequence set forth in SEQ. ID. NO:7 or SEQ. ID. NO:37, and the variable heavy chain of the humanized antibody may have the amino acid sequence set forth in SEQ. ID. NO:8, SEQ. ID. NO:9, or SEQ. ID. NO:38. In certain embodiments, the polynucleotide may include the sequence set forth in SEQ. ID. NO:29, while in other embodiments it may include the sequence set forth in SEQ. ID. NO:30. In certain embodiments, the polynucleotide may be part of a vector, and in certain of these embodiments the vector may be contained within a host cell.

In certain embodiments, a method is provided for treating a tumor that expresses PSCA by administering to a subject a humanized antibody that combines a human or humanized immunoglobulin framework with a binding site that recognizes the same epitope as murine monoclonal antibody 1G8. In certain embodiments, the humanized antibody may be bound to a conjugate such as a toxin, a cytokine, a chemotherapeutic agent, or a radiolabel. In certain embodiments, the tumor being treated may be a bladder tumor or a prostate tumor.

In certain embodiments, methods are provided for detecting or localizing a tumor that expresses PSCA by administering to a subject a radiolabeled humanized antibody that combines a human or humanized immunoglobulin framework with a binding site that recognizes the same epitope as murine monoclonal antibody 1G8, and scanning the subject with a photoscanner to detect the activity of the humanized antibody.

In certain embodiments, a composition is provided for detecting, localizing, or treating a tumor that expresses PSCA that includes a humanized antibody combining a human or humanized immunoglobulin framework with a binding site that recognizes the same epitope as murine monoclonal antibody 1G8.

BRIEF DESCRIPTION OF THE DRAWINGS

FIG. 1: Sequence alignment of 1G8 variable light ($V_L$) and variable heavy ($V_H$) domains with the 1QOK modeling template.

Lane 3=293T-PSCA. The blot was incubated with ch1G8 and anti-human IgG AP-conjugated antibodies were used for detection. Molecular weight standards appear next to lane 3. D. SDS-polyacrylamide gel electrophoresis of purified mu1G8 (lane 1), hu1G8-A (lane 2) and hu1G8-B (lane 3) under non-reducing conditions and reducing conditions. E. Flow cytometry. Purified mu1G8, hu1G8-A and hu1G8-B were assayed for binding to LNCap-PSCA cells and detected with Alexa-488 conjugated anti-mouse and anti-human IgG antibodies. F. Competitive ELISA binding assay using biotinylated intact mu1G8 monoclonal antibody as tracer and increasing amounts of unlabeled competitors, i.e., mu1G8, hu1G8-A and hu1G8-B.

Figure 4:
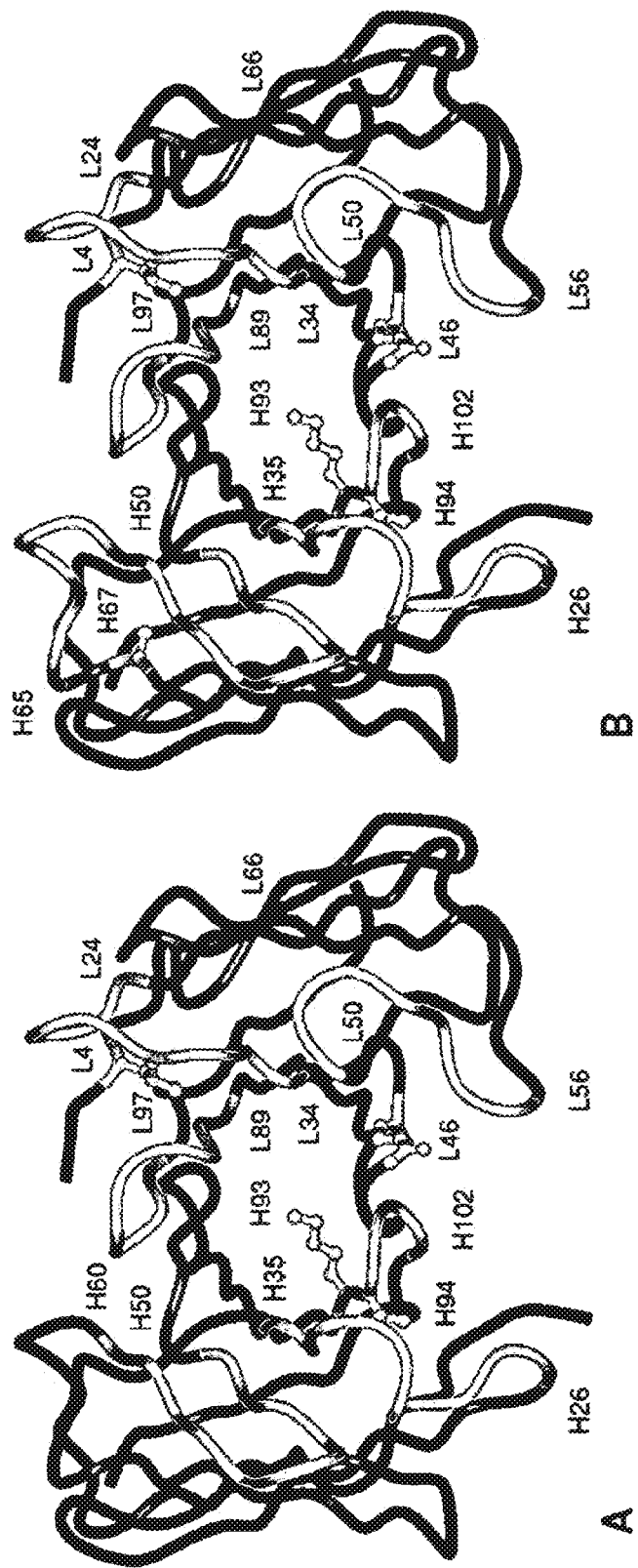

FIG. 4: Ribbon rendering of hu1G8-A (A) and hu1G8-B (B) models. Black segments represent human residues taken from 4D5 version 8 coordinates. White segments represent murine residues taken from 1G8 coordinates. Segment boundaries are labeled with residue numbers. Residues rendered in ball-and-stick are framework residues that were back mutated to their murine counterparts.

FIG. 5: Structure-based sequence alignment of mu1G8 variable light ($V_L$) and variable heavy ($V_H$) domains with 4D5 version 8 (Herceptin), hu1G8-A, and hu1G8-B. Peptide segments of murine origin are shown in bold typeface. Sequences and CDR boundaries are numbered according to Kabat. Note that the segments that were transplanted from donor to acceptor to create hu1G8-A and hu1G8-B model do not necessarily correspond to Kabat CDRs.

Figure 6:
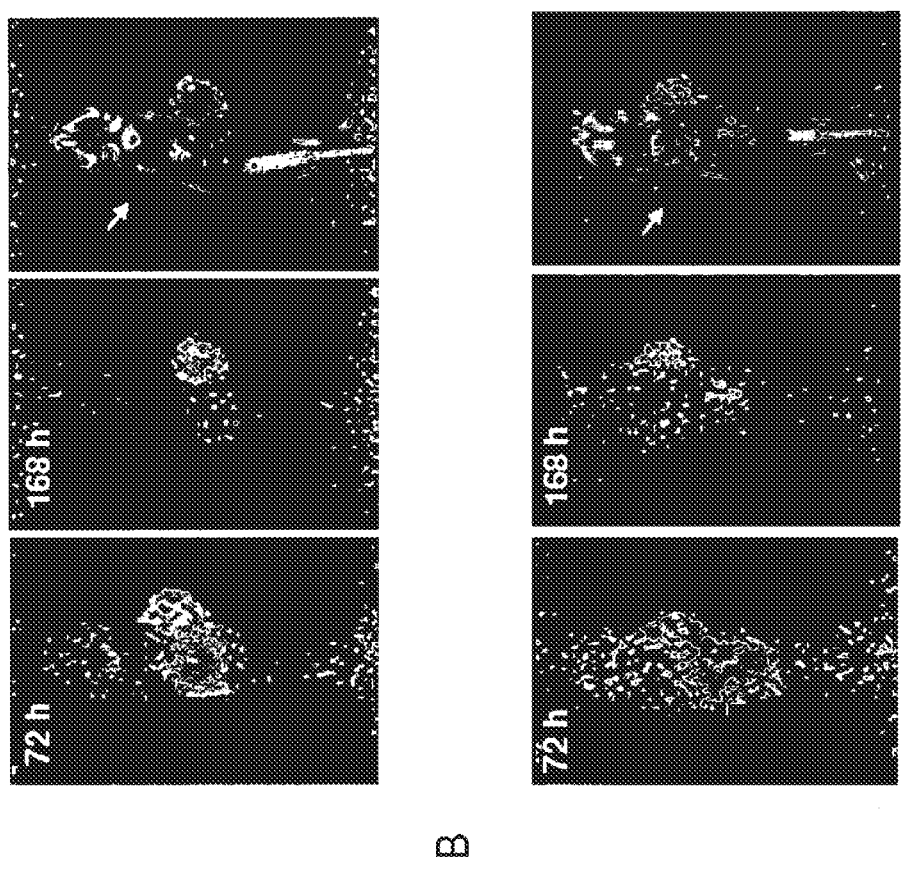

FIG. 6: Coronal microPET scan images (4 mm thick slices) and microPET/CT fused images of $^{124}$I-labeled anti-PSCA antibodies in individual SCID mice bearing LAPC-9 (antigen positive) and PC3 (antigen negative) xenografts at 72 hours and 168 hours. A. Coronal view of a SCID mouse given 127 μCi 124I-mu1G8. B. Coronal view of a SCID mouse given 110 μCi $^{124}$I-hu1G8-B. The negative tumor is indicated by an arrow in the microPET/CT fused images.

Figure 7:
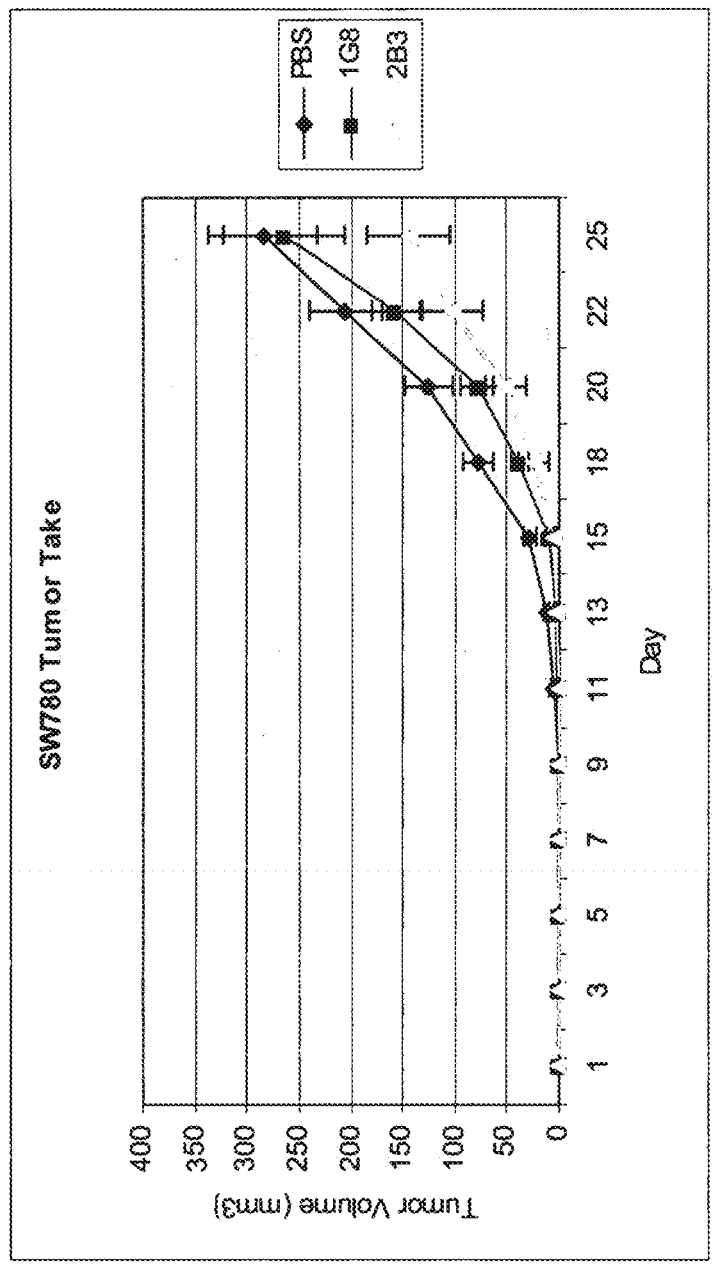

FIG. 7: Inhibition of tumor take of SW780 bladder carcinoma cells in SCID mice by mu1G8 and hu1G8-B (clone 2B3).

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

DEFINITIONS

The term "antibody" as used herein refers to any immunoglobulin, including antibodies and fragments thereof, that binds to a specific antigen. The term encompasses polyclonal, monoclonal, chimeric, humanized, and bispecific antibodies, and may refer to an intact immunoglobulin molecule or to some immunologically active portion of an immunoglobulin molecule, such as a Fab, Fab', F(ab')$_2$, or Fv portion. A complete antibody comprises two heavy chains and two light chains. Each heavy chain consists of a variable region and a first, second, and third constant region, while each variable chain consists of a variable region and a constant region. The antibody has a "Y" shape, with the stem of the Y consisting of the second and third constant regions of two heavy chains bound together via disulfide bonding. Each arm of the Y consists of the variable region and first constant region of a single heavy chain bound to the variable and constant regions of a single light chain.

The phrase "humanized antibody" as used herein refers to a genetically-engineered antibody wherein the variable region comprises the CDRs or portions of the CDRs of a non-human antibody and the framework regions of a human antibody, and the constant region comprises the constant region of a human antibody.

The term "epitope" as used herein refers to the specific group of atoms on an antigen molecule to which a specific antibody binds, causing an immune response.

The term "acceptor" as used herein refers to a molecule that provides the structural framework for creation of a humanized molecule, such as a human immunoglobulin.

The term "donor" as used herein refers to the molecule that provides the binding site element of a humanized molecule. This molecule is generally a non-human polypeptide, such as a murine monoclonal antibody.

The term "polypeptide" as used herein refers to any peptide or protein comprising two or more amino acids joined to each other by peptide bonds or modified peptide bonds, i.e., peptide isosteres. "Polypeptide" refers to both short chains, commonly referred to as peptides, oligopeptides, or oligomers, and to longer chains, generally referred to as proteins. Polypeptides may contain amino acids other than the gene-encoded amino acids. "Polypeptides" include amino acid sequences modified by natural processes, such as posttranslational processing, or by chemical modification using techniques that are well known in the art. Such techniques have been described in basic texts, more detailed monographs, and voluminous research literature. Modifications can occur anywhere in a polypeptide, including the peptide backbone, the amino acid side-chains, and the amino or carboxyl termini. One skilled in the art will recognize that the same type of modification may be present in the same or varying degrees at several sites in a single polypeptide, and that a single polypeptide may contain multiple modifications. Polypeptides may be branched as a result of ubiquitination, and they may be cyclic, with or without branching. Cyclic, branched, and branching cyclic polypeptides may result from posttranslational natural processes, or they may be created by synthetic methods. Polypeptide modifications include acetylation, acylation, ADP-ribosylation, amidation, attachment of an antibody Fc domain (native, recombinant, or humanized), biotinylation, carboxymethylation, covalent attachment of flavin, covalent attachment of a heme moiety, covalent attachment of a lipid or lipid derivative, covalent attachment of a nucleotide or a nucleotide derivative, covalent attachment of phosphotidylinositol, cross-linking, cyclization, dansylation, demethylation, disulfide bond formation, enzyme labeling, farnesylation of cysteine residues, FITC-conjugation, formation of covalent cross links, formation of cystine, formation of pyroglutamate, formylation, gamma-carboxylation, glycosylation, GPI anchor formation, hydroxylation, iodination, methylation, myristoylation, oxidation, pegylation, phosphorylation, prenylation, proteolytic processing, racemization, radiolabeling, selenoylation, succinylation, sulfation, transfer-RNA mediated addition of amino acids to proteins such as arginylation, and ubiquitination. See, for example, Proteins—Structure and Molecular Properties, 2$^{nd}$ Ed., T. E. Creighton, W.H. Freeman and Company, New York, 1993; Wold, F., "Posttranslational Protein Modifications: Perspectives and Prospects," pgs. 1-12 in Posttranslational Covalent Modification of Proteins, B. C. Johnson, Ed., Academic Press, New York, 1983; Seifter, S., Englard, S. 1990. Analysis for protein modifications and nonprotein cofactors. Meth Enzymol 182:626-646; Rattan, S. I., Derventzi, A., Clark, B. F. 1992. Protein synthesis: posttranslational modifications and aging. Ann N Y Acad Sci 663:48-62.

The term "polynucleotide" as used herein refers to any polyribonucleotide, polydeoxyribonucleotide, or hybrid polyribo-polydeoxyribonucleotide, including naturally occurring polynucleotides, synthetic polynucleotides, or any chemically, enzymatically, or metabolically modified forms of naturally occurring polynucleotides. Polynucleotides may contain any of the standard pyrimidine or purine bases (i.e., adenine, guanine, cytosine, thymine, uracil), as well as any modified or uncommon bases such as tritylated bases or inosine. In addition, the backbone of a polynucleotide may be modified for stability or for other reasons.

The phrase "coding sequence" as used herein refers to a polynucleotide sequence having sequence information necessary to produce a gene product for which expression is desired, according to normal base pairing and codon usage relationships. In order to produce this gene product, the coding sequence must be placed in such relationship to transcriptional control sequences (possibly including control elements and translational initiation and termination codons) that a proper length transcript will be produced and will result in translation in the appropriate reading frame to produce a functional desired product.

The term "isolated" as used herein means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. "Isolated" as used herein does not exclude artificial or synthetic mixtures with other compounds or materials, or the presence of impurities that do not interfere with activity.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, and artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which a vector has been introduced. A host cell may be selected from a variety of cell types, including for example bacterial cells such as *E. coli* or *B. subtilis* cells, fungal cells such as yeast cells or *Aspergillus* cells, insect cells such as *Drosophila* S2 or *Spodoptera* Sf9 cells, or animal cells such as fibroblasts, CHO cells, COS cells, NSO cells, HeLa cells, BHK cells, HEK 293 cells, or human cells.

The phrase "scanning device" as used herein refers to any device for detecting a radionuclide or fluorescent agent, such as a photoscanner for detecting radioactive activity. More specifically, "scanning device" refers to a device capable of detecting the presence of a radionuclide that has been injected in a subject, identifying the specific location of the radionuclide within the subject, and quantifying the amount of radionuclide within that specific location.

Abbreviations

The following abbreviations are used herein: CDR, complementarity determining region; HAMA, human anti-murine antibody; mAb, monoclonal antibody; PSCA, prostate stem cell antigen; SCID, severe combined immune deficient; SDS-PAGE, sodium dodecyl sulfate polyacrylamide gel electrophoresis; $V_H$, variable heavy; $V_L$, variable light.

Humanized 1G8 Antibodies

Prostate cancer is an attractive target for antibody-based therapy for several reasons: 1) tissue-specific rather than tumor-specific targeting is allowed as the prostate is a non-essential organ; 2) metastases are usually small enough to enable good penetration; 3) the metastases that primarily involve bone marrow and lymph nodes are in locations that receive high levels of circulating antibody; 4) therapeutic effect can be rapidly monitored by serum prostate-specific antigen (PSA); and 5) prostate cancer is radiation sensitive, rendering it an excellent target for radiolabeled antibody therapies.

Several mAbs targeting general tumor antigens or prostate specific antigens have been developed that are in preclinical and clinical development (Maynard 2000; Smith-Jones 2004). However, human anti-mouse antibody (HAMA) responses, dose limiting toxicity, and low therapeutic efficacy are issues that have been reported.

One solution to HAMA response problem is to generate human antibodies from human immunoglobulin phage display libraries (Winter 1994) or transgenic animals (Bruggemann 1991, Mendez 1997). These techniques have produced a small yet growing number of antibodies with high specificity and affinity. However, antibodies produced by these methods have either exhibited specificity only for immobilized antigen or have exhibited poor expression as intact antibodies in mammalian cell culture. Another solution to the HAMA response problem has been the use of recombinant methodologies to generate chimeric monoclonal antibodies, which generally consist of a murine antigen-binding variable domain coupled to a human constant domain. These chimeras have a lower frequency of immune response, but they are not effective for all antibodies and may still generate an immune response against the murine variable region. A third solution to the HAMA response problem is the utilization of humanized or reshaped monoclonal antibodies. These consist of human antibodies in which only the complementarity determining region (CDR) has been substituted with an animal CDR.

The current generation of humanized monoclonal antibodies that have been approved for therapy are the result of grafting murine-derived CDR's onto a human antibody framework (Jones 1986; Low 1986). This process of CDR-grafting is a well established technique, but it has a downside in that it frequently generates an antibody with substantially decreased antigen binding affinity compared to the parental antibody. This decreased affinity is the result of unanticipated steric clashes between the human immunoglobulin framework and the murine CDR side chains, which alter the CDR loop conformation. This disadvantage can be overcome by the reiterative process of back-mutagenesis, which involves the restoration of key murine framework residues that are responsible for maintaining the correct CDR loop conformations (Foote 1992). However, this process is laborious and random.

There are many examples in the published literature of antibody humanization via CDR-grafting (O'Brien 2003). However, this process often results in an antibody with substantially decreased binding affinity compared to the parental antibody. This decreased affinity is caused by unanticipated steric clashes between the human immunoglobulin framework and the mouse CDR residues, which alter the conformation of the antigen binding loops. Such steric clashes can be overcome by introducing back-mutations to restore key murine framework residues responsible for correct loop conformation, but this process is laborious and often reiterative (Foote 1992). The reason steric clashes in humanized antibodies have been unanticipated is because the constructs have been designed using molecular models of the graft donor and graft acceptor molecules, rather than actual crystal structures of one or both of those molecules. For instance, donor and acceptor molecules have previously been selected based on their amino acid sequences (U.S. Pat. Nos. 5,639,641; 6,639,055). In these approaches, the amino acid sequences of exposed regions of the murine antibody are obtained, and sequence databases are used to select a human antibody with the same or a similar sequence.

Prostate stem cell antigen (PSCA) is a predominantly prostate-specific cell surface antigen that is expressed in the majority of prostate cancer patients (Reiter 1998; Gu 2000; Reiter 2000). PSCA is a cysteine-rich 123 amino acid glycosylphosphatidylinositol (GPI)-anchored surface glycoprotein related to the Thy-1/Ly-6 family (Reiter 1998). Studies have shown PSCA expression in 80% of local disease and in all bone metastatic lesions examined (Reiter 1998; Gu 2000). Elevated PSCA expression has been correlated with increased tumor stage, grade, and progression to androgen dependence (Gu 2000). The high expression level of PSCA in cancerous tissue, combined with its low expression in normal tissue, makes it an ideal target for immunotherapy.

Several antibodies were raised previously against a PSCA-GST fusion protein (Gu 2000). Five of these antibodies (1G8, 4A10, 3E6, 3C5, and 2H9) were subcloned, purified, and shown to bind PSCA by flow cytometry. Their epitope localization on PSCA was determined and classified into three regions: 4A10, 2H9, and 3C5 bound to a region close to the N-terminus (aa 21-50); 1G8 bound to the middle region (aa 46-85), and 3E6 bound to a region close to the C-terminus (aa 85-99). Two of these anti-PSCA mAbs, 1G8 (IgG1κ; $K_D=1$ nM) and 3C5 (IgG2aκ; $K_D=43$ nM) were examined for their inherent anti-tumor efficacy in subcutaneous and orthotopic prostate cancer xenografts models (Saffran 2001). Although both antibodies demonstrated similar anti-tumor activity, 1G8 was consistently more efficacious than 3C5 in growth retardation of orthotopic tumors, which lead to greater prolongation of survival. This superiority was attributed to higher affinity, isotype, and/or the localization of the epitope on PSCA. However, it has recently been shown that F(ab')$_2$ alone can exert this effect, suggesting that Fc is not required (Gu 2005).

Biodistribution studies of 1G8 radiolabeleled with $^{111}$In are presented herein, and specific tumor targeting is demonstrated. However, the utility of 1G8 in human immunotherapy is likely to be limited due to immunogenicity and the potential of the antibody to generate a HAMA response. Thus, chimeric and humanized 1G8 antibodies have been developed in order to generate 1G8 with substantially reduced immunogenicity.

Murine 1G8 variable genes were isolated and fused to human κ and IgG1 constant genes to produce anti-PSCA mouse-human chimeric 1G8 (ch1G8). Although ch1G8 retained the binding specificity of parental antibody and demonstrated improved in vivo efficacy over mu1G8 in a prostate cancer model, it expressed at low levels and was unstable in PBS. Since it is well known that chimeric antibodies can induce an immune response in humans when administered repeatedly, a humanized mu1G8 antibody was generated to improve stability and expression and reduce immunogenicity.

Humanized 1G8 (hu1G8) was generated using a CDR grafting strategy. Since the crystal structure of 1G8 was not yet available, a molecular model of the Fv region of 1G8 was created using the anti-CEA antibody MFE-23 (PDB file 1QOK) as a template. 1QOK was chosen as the sole modeling template because it shares high sequence identity with 1G8, five of its six hypervariable loops are of the same length as those of 1G8, and the two chains form a cognate pair, which greatly increases the accuracy of the modeled $V_L$:$V_H$ interface.

Antibody 4D5 version 8 (hu4D5v8) was chosen as a suitable framework provider based largely on its remarkably low immunogenicity: only 0.5% of breast cancer patients participating in a large-scale multinational trial developed HAHA (Cobleigh 1999). This phenomenon may be related to the fact that the $V_H$ and $V_L$ regions of 4D5v8 are derived from the two most common human germline gene families, namely the $V_H$3 family, which constitutes 43% of all human $V_H$ germline genes, and the Vκ1 family, which constitutes 25% of all human $V_L$ germline genes (Ewert 2003). In addition, the 4D5v8 framework has been extensively characterized, is known to be stable, and exhibits a high degree of structural similarity to the molecular model of 1G8 discussed above.

Previous studies have used 4D5v8 as a framework provider for humanization of the anti-CEA mAb T84.66 (Yazaki 2004). In those studies, two versions (A and B) of the construct were created because it was uncertain whether the C-terminal end of CDR-H2 (H60-H65) made contact with antigen and therefore had to be carried over into the graft. For huT84.66, the identity of residues in this region proved to be unimportant; when purified and assayed, both versions exhibited the same affinity (Yazaki 2004). For mu1G8, it was reasonable to assume the opposite, i.e., that these residues might be critical for antigen recognition since CDR-L1 and CDR-H3 are both truncated, leaving CDR-H2 highly exposed.

Two humanized 1G8 antibodies, hu1G8-B (M6B) and hu1G8-A (M6A), were created. In both hu1G8-B and hu1G8-A, six peptide segments corresponding approximately with CDR-L1, CDR-L2, CDR-L3, CDR-H1, CDR-H2, and CDR-H3 were deleted from the hu4D5v8 framework molecule and replaced with corresponding murine peptide segments from 1G8. With regards to these segments, the only difference between hu1G8-A and hu1G8-B was five extra CDR-H2 residues replaced with their murine equivalents in hu1G8-B. In hu1G8-B, two additional hu4D5v8 residues were replaced with their murine equivalent to minimize steric hindrance between donor and acceptor side chains, while in hu1G8-A only one of these residues was replaced with its murine equivalent. In both hu1G8-B and hu1G8-A, four additional hu4D5v8 residues were replaced with their murine equivalent based on potential effects on antigen binding.

Fully synthetic genes encoding the $V_L$ chain and $V_H$ chains of hu1G8-A and hu1G8-B were created using splice overlap extension polymerase chain reaction. Purified full-length $V_L$ chain genes were ligated into the expression plasmid pEE12, while $V_H$ chain genes were ligated into the expression plasmid pEE6. Both of these plasmids had been previously modified to contain the cDNA sequence of the corresponding constant regions of a human $IgG_1$ antibody. The heavy chain gene was then removed from pEE6 and ligated into the pEE12 light chain plasmid. This dual chain pEE12/6 plasmid was electroporated into murine myeloma NS0 cells, and transfectants were screened for secretion of humanized 1G8 using ELISA. The hu1G8-B and hu1G8-A clones with the highest expression levels were expanded. SDS-PAGE analysis of purified aliquots of hu1G8-B and hu1G8-A under reducing conditions revealed two bands corresponding to the light and heavy chain polypeptides, while ELISA and FACS analysis confirmed that both humanized antibodies specifically bound PSCA. The hu1G8-B antibody, which includes more murine residues in CDR-H2 than hu1G8-A, demonstrated a six-fold higher relative binding affinity to PSCA compared to hu1G8-A. Thus, it appears that for this particular antibody, the C-terminal end of CDR-H2 makes contact with antigen.

Although the binding affinity of hu1G8-B for PSCA was about five-fold lower than that of mu1G8, its ability to target tumor was equivalent when evaluated by microPET imaging. In addition, studies in nude mice with bladder carcinoma suggest that the in vivo efficacy of hu1G8 is superior to that of the parental mu1G8. It has recently been shown that mu1G8 acts by a direct Fc-independent mechanism to inhibit prostate tumor growth both in vivo and in vitro (Gu 2005). However, since nude mice have some immune effector cells, engagement of the mouse immune system such as antibody dependent cellular cytotoxicity (ADCC) and/or complement-dependent cytotoxicity (CDC) brought on by switching from mouse to human IgG1 isotype may also play a factor in inhibiting tumor growth in this model. The lower activity of both antibodies in the tumor at a later time point (168 hours vs. 94 hours i.e. at the time of sacrifice in the two microPET studies) is probably due to the active internalization of the 1G8. Upon internalization, radioiodinated antibodies become proteolytically degraded into iodotyrosines that are rapidly deiodinated resulting in fast disappearance of the radioactivity (Geissler 1992; Xu 1997).

The 1G8 molecular model was further refined using the crystal structures of additional antibodies with CDR loops very similar or identical to those of 1G8. Based on the overlap of this refined model with hu4D5v8, six additional hu1G8-B residues were selected for back mutation to the corresponding murine residue to create hu1G8-C (M6C). The purpose of these back mutations was to increase the PSCA binding affinity of the humanized antibody to that of the murine 1G8 antibody.

The humanized antibodies of this invention may be conjugated with small molecule toxins, cytokines, or chemotherapeutic agents (e.g., doxurubicin) for specific delivery to cancer cells. In addition, binding of the humanized antibodies to tumor cells may be used to recruit host immune responses. This host immune response may be increased by utilizing bivalent antibodies, with one binding site corresponding to the humanized construct of the present invention and another binding site that recognizes cytotoxic T-cells.

The humanized antibody of the present invention may be administered for detection or treatment of PSCA expressing tumors by subcutaneous, peritoneal, intravascular, intramuscular, intradermal or transdermal injection, among other methods. The antibody may be labeled with a variety of labeling agents, including radioactive labels such as iodine ($^{123}$I, $^{124}$I, $^{125}$I, $^{131}$I), sulfur ($^{35}$S), tritium ($^{3}$H), indium ($^{111}$In, $^{112}$In), carbon ($^{14}$C), copper ($^{64}$Cu, $^{67}$Cu), yttrium ($^{86}$Y, $^{88}$Y, $^{90}$Y), lutitium ($^{177}$Lu), other lanthanides, luminescent labels, or fluorescent labels, or some combination thereof. Those of skill in the art will recognize that a variety of conjugates may be coupled to the humanized antibody (see, for example, "Conjugate Vaccines", Contributions to Microbiology and Immunology, J. M. Cruse and R. E. Lewis, Jr. (eds.), Carger Press, New York, (1989)). These conjugates may be linked to the humanized antibody by covalent binding, affinity binding, intercalation, coordinate binding, or complexation, among other methods. Conjugates may also consist of chemotherapeutic agents such as vindesine, cisplatin, doxurubicin, or adriamycin, or any other compound useful in the treatment of cancer, or toxins such as ricin or diptheria toxin, among others.

For detection and localization of tumors expressing PSCA, the humanized antibody of the present invention will be administered at a dose sufficient for detection by a scanning device. This dosage will be dependent on the type of label being used. The type of scanning device to be used will vary depending on the label being used, and one skilled in the art will easily be able to determine the appropriate device.

For treatment of tumors expressing PSCA, the humanized antibody of the present invention may be prepared at an effective dose as a formulation within pharmaceutically acceptable media. This formulation may include physiologically tolerable liquids, gels, solid carriers, diluents, adjuvants, or excipients, or some combination thereof. The pharmaceutical formulation containing the humanized antibody may be administered alone or in combination with other known tumor therapies. Effective dosage will depend in part on the weight, age, and state of health of the subject, as well as the administration route and extent of tumor development.

The humanized antibody of the present invention or portions thereof may be expressed using any appropriate expression system. Polynucleotides encoding variable light ($V_L$) and variable heavy ($V_H$) chains of the humanized antibody may be expressed using separate vectors, or both chains may be expressed from one vector. Suitable vectors may contain a variety of regulatory sequences, such as promoters, enhancers, or transcription initiation sequences, as well as genes encoding markers for phenotypic selection. Such additional sequences are well known in the art. Additionally, the vector may contain a polynucleotide sequence encoding the constant regions of the heavy chain ($C_H$) and light chain ($C_L$) of a human immunoglobulin. Alternatively, the vector may express only the $V_H$ and $V_L$ chains of the humanized antibody, with the expressed polypeptide comprising an Fv fragment rather than a whole antibody.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Construction and Expression of Chimeric 1G8 (ch1G8)

ch1G8 was constructed using a procedure similar to that described previously by Coloma et al. (Coloma 1992).

mu1G8 hybridoma cells (Gu 2000) from American Tissue Culture Collection (ATCC No. HB-12612, deposited Dec. 11, 1998; ATCC, Manassas, Va.) were grown in Iscove's Modified Dulbecco's Medium (IMDM)/5% FBS. Total RNA was extracted from the cells using ULTRASPEC® Total RNA Isolation Reagent (Biotecx Laboratories, Houston, Tex.). First strand DNA synthesis (cDNA) was prepared from total RNA using GENEAMP® RNA PCR kit and oligo d(T)$_{16}$ as primer (Roche Applied Biosystems, Foster City, Calif.). The variable heavy ($V_H$) and light ($V_L$) chain genes were amplified from cDNA using primer sequences described by Coloma et al. (Coloma 1992). PCR products were cloned into pCR2.1 (Invitrogen Life Technologies, Carlsbad, CA) and several clones were sequenced. In order to verify that the sequences were correct, the primary amino acid sequences were compared to tryptic peptide sequences of the intact, parental mu1G8 mAb heavy and light chains as described (Wu 2001).

The mu1G8 $V_L$ gene was cloned into the human κ light chain expression vector pAG4622 using EcoRV and SalI restriction sites. The mu1G8 $V_H$ gene was cloned into the human IgG1 heavy chain expression vector pAG3021 via EcoRV and NheI restriction sites. Linearized 1G8 light chain vector was electroporated into P3×63.Ag8.653 non-producing myeloma cells grown in Iscove's Modified Dulbecco's Medium (IMDM)/5% FBS. Cells were selected in media supplemented with xanthine, mycophenolic acid and hypoxanthine (XMH). High expressing clones were identified by ELISA of the culture supernatants using goat anti-human κ alkaline phosphate-conjugated antibodies (Jackson ImmunoResearch Laboratories, West Grove, Pa.). Cells expressing high levels of ch1G8 light chain were electroporated with linearized ch1G8 heavy chain vector and selected in presence of histidinol. Secretion of ch1G8 to the cell culture supernatant was measured by ELISA using goat anti-human IgG (Fc specific) to capture ch1G8 constructs and alkaline-phosphatase-conjugated goat anti-human IgG (Fc specific) antibodies (both from Jackson ImmunoResearch Laboratories) for detection. The best producing clones were further evaluated by Western blot for size verification. High producing clones were expanded into TripleFlasks (Nalge Nunc Int'l, Rochester, N.Y.) or into CELL-PHARM® 100 hollow fiber cell culture system (Unisyn Technologies, Hopkinton, Mass.) in 1MDM/1% FBS supplemented with GLUTAMAX® (Invitrogen Life Technologies). The expression level of ch1G8 in the highest producing clone was only about 2-3 μg/mL in TripleFlasks.

Example 2

Development of a Murine 1G8 Humanization Design

Homology modeling preceded humanization since no crystal structure was available for the mu1G8 Fv region. A crystallographic template suitable for modeling this region was selected by performing a sequence-based search of the Protein Data Bank (Berman 2002) using the FASTA program (Pearson 1988). Anti-CEA antibody MFE-23 (PDB file 1QOK) (Boehm 2000) was chosen as a template for modeling 1G8 for three reasons: 1) the percent sequence identity was high (81% for $V_L$, 80% for $V_H$); 2) with the exception of the CDR-H3 loop, the lengths of the hypervariable loops were identical and oftentimes the actual sequences were identical or nearly identical; and 3) the $V_L$ and $V_H$ templates formed a cognate pair. The amino acid sequences of the $V_L$ and $V_H$ chains of 1G8 are set forth in SEQ. ID. NOs: 1 and 2, respectively, while the amino acid sequence of the $V_L$ and $V_H$ chains of 1QOK are set forth in SEQ. ID. NOs: 3 and 4, respectively. The amino acid sequence alignment of the $V_L$ and $V_H$ chains of 1G8 and 1QOK is shown in FIG. 1.

The HOMOLOGY module within INSIGHT II® (Accelrys, San Diego, Calif.) was used to construct the molecular model. CDR-H3 was modeled by deleting residues H96-H100c from the template and forming a peptide bond between residues H95 and H101.

After repositioning the side chains of residues L46, L90, and L95 to eliminate steric clashes, the stereochemistry of the model was improved using conjugate gradients energy minimization until the maximum derivative was less than 5 kcal/mol-Å.

Figure 2:
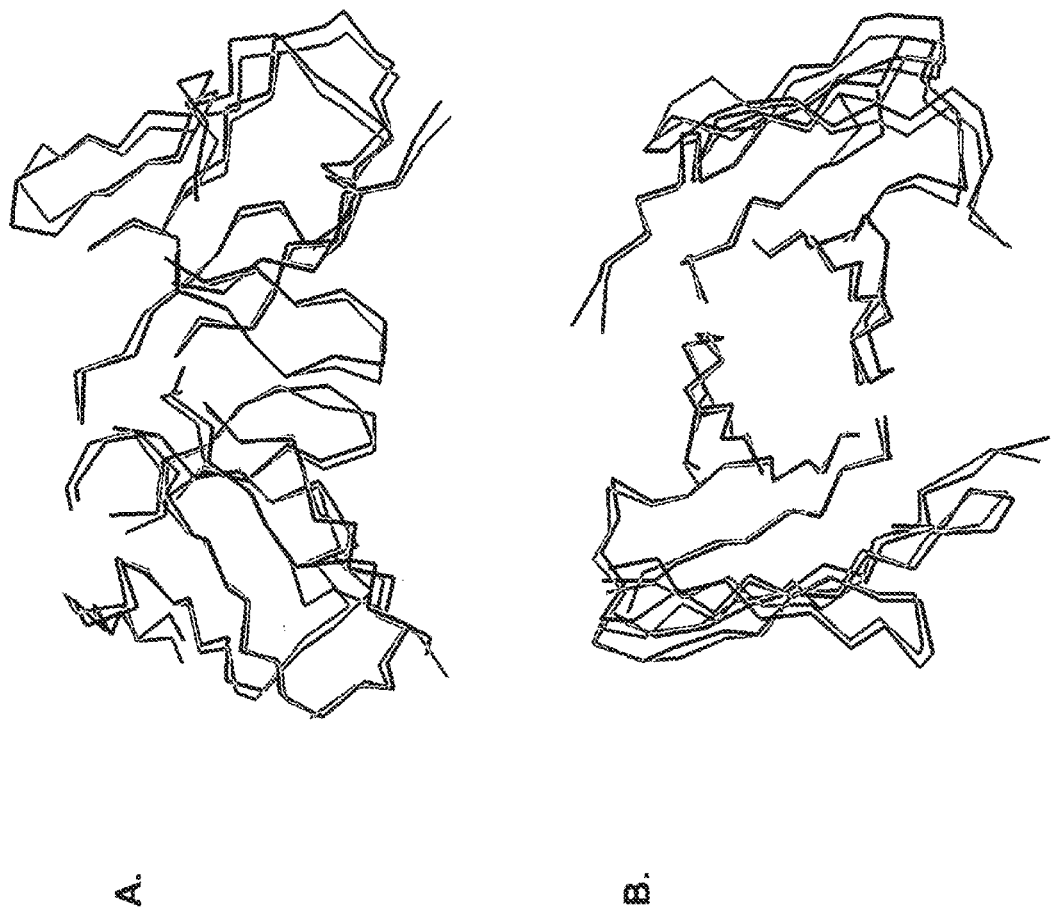
FIG. 2: Superimposed alpha carbon traces of 1G8 (black) and 4D5 version 8 (gray) framework regions. Two orthogonal views (A and B) are shown.

CDR-grafting was selected as a suitable strategy for humanizing 1G8 (Jones 1986; Low 1996). Humanized antibody 4D5 version 8 (hu4D5v8, anti-p185$^{HER2}$, HERCEPTIN® (Trastuzumab), PDB file 1FVC) (Eigenbrot 1993) was selected as the most appropriate framework provider for the proposed CDR graft based on previous success using this Fv for humanization (Yazaki 2004). The degree of overlap between hu4D5v8 and the 1G8 model was very high (root-mean-square deviation of 1.07 Å for 1320 backbone atoms), and the angle of $V_L$-$V_H$ domain pairing was essentially the same as seen from two orthogonal views of the superimposed alpha carbon traces in FIG. 2. The amino acid sequences of the $V_L$ and $V_H$ chains of hu4D5v8 are set forth in SEQ. ID. NOs: 5 and 6, respectively.

Using the HOMOLOGY module, the Kabat CDRs of the 1G8 model were grafted onto the hu4D5v8 framework. The CDR graft strategy is shown by sequence alignment in FIG. 5. Visual inspection of the superimposed structures suggested that minimal disruption of the CDR loops could be achieved by deleting six peptide segments from the hu4D5v8 graft acceptor structure (Kabat residues L24-L34, L50-L56, L89-L97, which correspond to residues 24-34, 50-56, and 89-97 of SEQ. ID. NO:5, and Kabat residues H26-H35, H50-H65, and H93-H102, which correspond to residues 26-35, 50-66, and 97-109 from SEQ. ID. NO:6) and replacing them with six corresponding peptide segments from the mu1G8 graft donor structure (Kabat residues L24-L34, L50-L56, L89-L97, which correspond to residues 24-33, 49-55, and 88-96 of SEQ. ID. NO:1, and Kabat residues H26-H35, H50-H65, and H93-H102, which correspond to residues 26-35, 50-66, and 97-101 of SEQ. ID. NO:2).

Upon completing the graft, the resulting molecular model was inspected for potential steric clashes between donor and acceptor side chains at the CDR-framework interface. A clash between hu4D5v8 framework residue L4 (methionine, residue 4 in SEQ. ID. NO:5) and mu1G8 CDR-L1 residue L33 (isoleucine, residue 32 in SEQ. ID. NO:1) was alleviated by replacing the hu4D5v8 L4 residue with the L4 residue from 1G8 (leucine, residue 4 in SEQ. ID. NO:1). A clash between hu4D5v8 framework residue H67 (phenylalanine, residue 68 in SEQ. ID. NO:6) and 1G8 CDR-H2 residue H63 (phenylalanine, residue 64 in SEQ. ID. NO:1) was alleviated by replacing the hu4D5v8 H67 residue with the H67 residue from 1G8 (alanine, residue 68 in SEQ. ID. NO:1).

The molecular model of hu1G8 revealed an unusual binding site topology, namely a cleft arising from a truncated CDR-L1 loop having ten residues rather than 11 and a severely truncated CDR-H3 loop having just three residues (FIG. 5). Because of these loop truncations and the fact that the tip of the CDR-H3 loop lacked side chains (sequence Gly-Gly), four framework residues gained the potential to interact with antigen: L46 (Arg), L66 (Gly), H93 (Lys), and H94 (Thr). All four of these residues were replaced with their murine equivalent in the humanized model. The resulting humanized structure, hu1G8-B, was subjected to an energy minimization algorithm (conjugate gradients to a maximum derivative of 5.0 kcal/mol-Å) to optimize bond lengths and angles at the splice junctions.

The binding site in the final model suggested that the C-terminal end of Kabat CDR-H2 (residues H60 to H65), which does not frequently make contact with antigen (Padlan 1995; MacCallum 1996), might indeed participate in antigen binding since CDR-L1 and CDR-H3 are truncated. For this reason, a second humanized 1G8, hu1G8-A, was created. In hu1G8-A, residues H60-H65 were treated as framework residues, meaning that they retained the amino acid sequence of hu4D5v8 (residues 61-66 of SEQ. ID. NO:6) rather than being replaced with the corresponding residues from 1G8. hu1G8-A also retains the hu4D5v8 framework residue at H67 (phenylalanine) that was replaced with alanine in hu1G8-B.

The amino acid sequence of the $V_L$ chain of hu1G8-A and hu1G8-B is set forth in SEQ. ID. NO:7. The amino acid sequences of the $V_H$ chains of hu1G8-A and hu1G8-B are set forth in SEQ. ID. NOs. 8 and 9, respectively. The structure-based sequence alignment of 1G8 $V_L$ and $V_H$ chains with hu4D5v8 (HERCEPTIN®), hu1G8-A, and hu1G8-B is shown in FIG. 5. A ribbon rendering of hu1G8-A and hu1G8-B is set forth in FIG. 4.

Example 3

Construction of Synthetic Genes Encoding hu1G8

Splice overlap extension polymerase chain reaction (SOE-PCR) (Horton 1989) using multiple overlapping oligonucleotides was used to synthesize hu1G8 $V_L$ and $V_H$ genes as previously described (Yazaki 2004). Eight oligonucleotides (Integrated DNA Technologies, Inc., Coralville, Iowa), ranging in size from 62 to 89 nucleotides, were required for each domain construct. The degree of overlap between adjacent oligonucleotides corresponded to 30 base pairs. The PCR primer sequences for the variable light ($V_L$) and variable heavy ($V_H$) domains are set forth in SEQ. ID. NOs:10-25.

Four sequential SOE-PCR amplifications were required to build each variable domain gene. The internal-most pair of primers (4 and 5) were amplified first. The resulting PCR product was gel purified and further extended with the next set of external primers (3 and 6). The third extension utilized primers 2 and 7, and the final extension utilized primers 1 and 8. Each 50 µL reaction contained reaction buffer, 2 units of Vent DNA Polymerase (New England Biolabs, Beverly, Mass.), amplification primers at 1 µM each, and dNTPs at 200 µM. Using a GeneAmp PCR 9600 thermocycler (Perkin Elmer, Wellesley, Mass.), samples were heated for 2 minutes at 94° C., followed by 30 cycles of heating for 30 seconds at 94° C., 30 seconds at 55° C., and 30 seconds at 72° C. After 30 cycles, the temperature was held constant at 72° C. for 10 minutes to ensure complete extension. In each case, the completed PCR reaction mix was electrophoresed on a 1% agarose gel (Sigma Chemicals, St. Louis, Mo.), and the desired product extracted from a 200 mg gel slice using a Qiaquik column (Qiagen, Valencia, Calif.). For the second, third, and fourth reactions, 10 ng of purified product from the preceding reaction was used as the template. The nucleotide sequences of the hu1G8-A/hu1G8-B $V_L$ chain, hu1G8-A $V_H$ chain, and hu1G8-B $V_H$ chain PCR products are set forth in SEQ. ID. NOs:26, 27, and 28, respectively. Each PCR product contains an engineered Fv region surrounded by short stretches of upstream and downstream sequences.

Individually, the purified PCR products were digested with Xba I and Xho I and ligated into one of two expression plasmids (pEE12 for $V_L$; pEE6 for $V_H$). These plasmids, which contain the Glutamine Synthetase (GS) gene (Lonza Biologics, Slough, UK; Bebbington 1992), had been previously modified to contain human κ and IgG1 constant cDNA genes, respectively. At this point, the entire gene (both variable and constant regions) was sequenced. The coding regions of the synthetic genes encoding the hu1G8-B $V_L$ and $V_H$ chains are set forth in SEQ. ID. NOs:29 and 30, respectively. In the pEE12 light chain plasmid, residue L104, whose codon is part of the XhoI restriction site, was mutated from leucine to valine using a Quik-Change kit (Stratagene, San Diego, Calif.) in order to restore the hu4D5v8 sequence in this region.

A dual chain plasmid was constructed by digesting the pEE6 heavy chain plasmid with BglII and Bam HI to isolate the heavy chain gene and ligating this gene into the BamHI site of the pEE12 light chain plasmid. The entire $IgG_1$ gene was sequenced in both directions to confirm its identity. Prior to electroporation the dual chain plasmid was linearized with Sal I, filtered through a protein binding membrane to remove the restriction enzyme (Millipore, Bedford, Mass.), ethanol precipitated, and resuspended in sterile water to a concentration of 1 µg/µl.

Example 4

Expression of hu1G8

NS0 murine myeloma cells were electroporated with the dual expression vector constructed in Example 3, and stable transfectants were selected by glutamine deprivation as described previously (Yazaki 2001a; Yazaki 2004). Secretion of hu1G8 to the cell culture supernatant was measured by ELISA using goat anti-human IgG (Fc specific) to capture hu1G8 constructs and alkaline-phosphatase-conjugated goat anti-human IgG (Fc specific) antibodies (both from Jackson ImmunoResearch Laboratories) for detection. The best producing clones were further evaluated by Western blot for size verification. High producing clones were expanded into TripleFlasks (Nalge Nunc Int'l, Rochester, N.Y.) or into CELL-PHARM® 100 hollow fiber cell culture system (Unisyn Technologies, Hopkinton, Mass.) in 1MDM/1% FBS supplemented with GLUTAMAX® (Invitrogen Life Technologies). Expression levels in these clones was at least 10-fold higher (10-30 µg/ml) than that of ch1G8 in Triple-Flasks, validating the predicted superiority of the hu4D5v8 framework.

Example 5

Purification of ch1G8 and hu1G8

Cell culture supernatants were harvested and passed over a Protein A column (Amersham Biosciences, Piscataway, N.J.) washed with 20 column volumes of PBS. Bound antibodies were eluted with 0.1 M glycine (pH 2.7) or with a pH gradient (pH 7.0 to pH 3.0) using 100 mM sodium phosphate/100 mM sodium citrate buffer. Eluted antibodies were immediately neutralized with 1M Tris-HCl (pH 9.0), pooled, and dialyzed against 150 nM NaCl/50 mM Tris-HCl (pH 8.0; ch1G8) or PBS (hu1G8) at 4° C. overnight. Antibodies were concentrated using Amicon Centriprep YM-10 (Millipore, Billerica, Mass.).

Example 6

Characterization of ch1G8 and hu1G8

Aliquots of purified ch1G8 and hu1G8 were analyzed by SDS-PAGE. ch1G8 was found to have a molecular weight of 150 kDa (FIG. 3A, lane 2), similar to that of parental mu1G8 (FIG. 3A, lane 1) under non-reducing conditions. Reducing conditions resulted in separation of the heavy (50 kDa) and light (25 kDa) chains. Both hu1G8-A (FIG. 3D, lane 2) and hu1G8-B (FIG. 3D, lane 3) migrated at the same weight as intact mu1G8 (FIG. 3D, lane 1) under non-reducing conditions. As with ch1G8, reducing conditions resulted in separation of the heavy (50 kDa) and light (25 kDa) chains.

Figure 3:
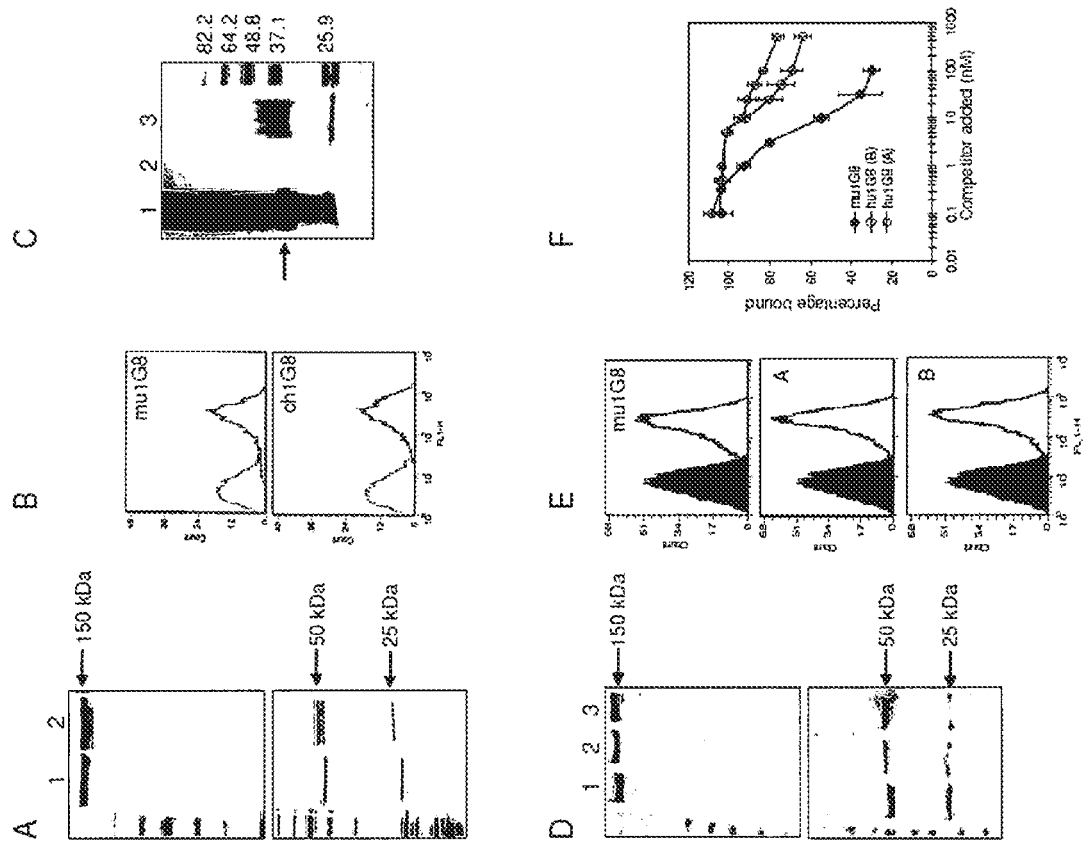
FIG. 3: Biochemical and functional characterization of purified 1G8 mAbs. A. SDS-polyacrylamide gel electrophoresis of purified mu1G8 (lane 1) and ch1G8 (lane 2) under non-reducing and reducing conditions. B. Purified mu1G8 and ch1G8 were assayed by flow cytometry for binding to LNCap-PSCA cells and detected with Alexa-488 conjugated anti-mouse and anti-human IgG antibodies. C. Western blot to demonstrate specific binding of ch1G8 to PSCA. Lane 1=GST-PSCA; Lane 2=293T negative control lysate.

Specific binding of the antibodies was analyzed by flow cytometry on LNCaP-PSCA cells and by Western blot using cell lysates from 293T cells transiently transfected with pcDNA3.0-PSCA. ch1G8 bound LNCaP-PSCA cells just as well as mu1G8 (FIG. 3B), and binding specificity to the antigen was confirmed by Western blot (FIG. 3C). ch1G8 was found to bind both bacterial expressed GST-PSCA (lane 1) and 293T-PSCA lysate (lane 3), whereas no binding was observed to 293T control cell lysate (lane 2). The lower molecular weight bands in lanes 1 and 3 represent truncated protein and unglycosylated PSCA, respectively. Both humanized antibodies demonstrated binding to LNCaP-PSCA that was equivalent to that of mu1G8 (FIG. 3E).

The relative binding affinities of the antibodies were measured by competitive ELISA using biotinylated mu1G8 as tracer. Wells were coated with soluble PSCA fused human IgG1 or mouse IgG2a Fc that had been expressed in pEE12 as described above and purified by Protein A affinity chromatography (Poros2.0; PerkinElmer, Wellesley, Mass.). A fixed concentration of biotinylated parental antibody and increasing concentrations of non-biotinylated competitors were used as previously described (Olafsen 2004). Detection of biotinylated antibody was made with alkaline phosphatase-conjugated streptavidin (Jackson ImmunoResearch Laboratories). A reduction in affinity was observed for both hu1G8 antibodies (FIG. 3F). The $K_D$ of mu1G8 was estimated to be 5 nM, versus 25 nM for hu1G8-B and 150 nM for hu1G8-A. Due to its superior binding affinity, hu1G8-B was selected for in vivo studies.

Example 7

Biodistribution Studies Using mu1G8

Purified mu1G8 was conjugated to pisothiocyanatobenzyldiethylenetriamine-pentaacetic acid (MX-DTPA or 1B4M-DTPA; Brechbiel 1991) as described previously (Olafsen 2005). Following conjugation, the protein was dialyzed extensively in 0.25 M NH$_4$OAc (pH 7.0) and concentrated. The MX-DTPA mu1G8 (0.32 mg) was incubated with 0.60 mCi of carrier free [$^{111}$In]chloride (Mallinckrodt Inc., Hazelwood, Mo.) in 0.25 M NH$_4$OAc (pH 7.0) for 45 minutes at room temperature. The reaction was terminated, labeled protein was purified by size-exclusion, and labeling efficiency (98.2%) and immunoreactivity (6%), measured by cell-binding to PC3-PSCA, were determined as described previously (Olafsen 2004; Yazaki 2001b). The $^{111}$In-MX-DTPA mu1G8 was used to perform a biodistribution study in nude male mice with PSCA xenografts. PC3-PSCA tumor xenografts were established by s.c. injection of 0.5-1×10$^6$ cells resuspended in 50% RPMI/50% MATRIGEL® (Becton Dickinson Labware, Bedford, Mass.) in the flanks of the mice. At about 14 days post-inoculation, mice bearing xenografts were injected with 3 µCi (1.6 µg protein) $^{111}$In-MX-DTPA mu1G8 via the tail vein. Time points analyzed were 0, 4, 12, 24, 48, 72, and 96 hours. Groups of five mice were euthanized at the different time points and radiouptakes in organs were measured. The percent of the injected dose per gram (% ID/g) with standard deviations (s.d.) was determined as previously described (Yazaki 2001b; Olafsen 2004). Results are summarized in Table 1, with tumor and normal organ uptake expressed as percent injected dose per gram (% ID/g). Tumor uptake reached a maximum of 17.1 (±6.7) % ID/g at 96 hours, with a tumor to blood ratio of 2.1. Hepatic uptake was 8.4 (±3.9) % ID/g at 96 hours, whereas the activity in other normal organs (spleen, kidney and lung) was lower.

TABLE 1

Biodistribution of $^{111}$In-MX-DTPA mu1G8 in nude mice bearing PC3-PSCA xenografts

|  | 0 h | 4 h | 12 h | 24 h | 48 h | 72 h | 96 h |
| --- | --- | --- | --- | --- | --- | --- | --- |
| Organ uptake (% ID/g) | | | | | | | |
| Tumor (T) | 0.52 | 2.28 | 6.87 | 11.80 | 13.15 | 13.75 | 17.11 |
|  | (0.17) | (0.70) | (1.90) | (3.07) | (6.41) | (4.00) | (6.67) |
| Blood | 31.91 | 21.86 | 15.89 | 13.69 | 10.84 | 7.49 | 8.01 |
|  | (2.54) | (1.28) | (2.15) | (0.97) | (2.32) | (3.30) | (3.06) |
| Liver | 7.48 | 8.41 | 6.56 | 7.79 | 7.39 | 9.21 | 8.36 |
|  | (1.12) | (1.78) | (1.45) | (1.16) | (2.32) | (3.17) | (3.92) |
| Spleen | 5.18 | 3.90 | 3.53 | 3.94 | 4.03 | 3.02 | 3.27 |
|  | (0.77) | (0.53) | (0.75) | (1.13) | (0.70) | (1.10) | (0.91) |
| Kidney | 4.52 | 4.95 | 4.50 | 3.95 | 3.16 | 2.36 | 2.25 |
|  | (0.61) | (0.74) | (1.05) | (0.94) | (0.68) | (0.63) | (0.53) |
| Lung | 8.60 | 7.54 | 6.01 | 5.21 | 4.92 | 3.23 | 4.96 |
|  | (0.61) | (1.19) | (1.41) | (0.88) | (0.85) | (1.44) | (1.58) |
| Carcass | 1.89 | 2.84 | 3.15 | 3.35 | 2.76 | 2.50 | 2.40 |
|  | (0.32) | (0.20) | (0.44) | (0.32) | (0.27) | (0.36) | (0.53) |
| Ratios | | | | | | | |
| T:Blood | 0.02 | 0.10 | 0.43 | 1.86 | 1.21 | 1.84 | 2.14 |
| T:Liver | 0.07 | 0.27 | 1.05 | 1.51 | 1.78 | 1.49 | 2.05 |
| T:Kidney | 0.12 | 0.46 | 1.53 | 2.99 | 4.16 | 5.83 | 7.60 |
| Tumor weight (g) | 0.089 | 0.097 | 0.094 | 0.092 | 0.121 | 0.148 | 0.114 |
|  | (0.033) | (0.030) | (0.022) | (0.042) | (0.036) | (0.052) | (0.042) |

Example 8

Tumor Targeting Using mu1G8 and hu1G8-B

Purified mu1G8 and hu1G8-B (0.2 mg each) were radioiodinated twice with the positron emitting isotope $^{124}$I (sodium iodide in 0.02 M NaOH; radionuclide purity >99%) provided by V. G. Khlopin Radium Institute & RITVERC GmbH (St. Petersburg, Russia) as previously described (Kenanova 2005). Instant thin layer chromatography using the Monoclonal Antibody ITLC Strips Kit (Biodex Medical Systems, Shirley, N.Y.) was used to determine the labeling efficiencies. The immunoreactivities were determined by cell binding assays. In the first radioiodination reaction, the labeling efficiencies were 81% and 94%, with immunoreactivities being 32% and 2%, for the mu1G8 and hu1G8, respectively. In the second reaction, the labeling efficiencies were 90% and 86% with immunoreactivities being 80% and 57% for the mu1G8 and hu1G8, respectively.

PC3-PSCA (antigen positive) and C6 (antigen negative) xenografts were established in nude mice as described above. Four mice were injected in the tail vein with 130-146 µCi of $^{124}$I-mu1G8 (specific activity=3.6 µCi/µg) or with 136-147 µCi of $^{124}$I-hu1G8 (specific activity=3.1 µCi/µg). Radiolabeled protein from the second labeling reaction was injected into male immunodeficient (SCID) mice (Taconic Farms, Germantown, N.Y.) with LAPC-9 (antigen positive) and PC-3 (antigen negative) xenografts. Three mice were injected in the tail vein with 127-134 µCi of $^{124}$I-mu1G8 (specific activity=2.0 µCi/µg) or with 107-111 µCi of $^{124}$I-hu1G8-B (specific activity=1.8 µCi/µg). At the indicated time points, mice were anesthetized with 2% isoflurane and imaged using a Focus microPET scanner (Concorde Microsystems Inc., Knoxville, Tenn.) as previously described (Kenanova 2005). Acquisition time was 10 minutes (1 bed position). Images were reconstructed using a filtered backprojection (FBP) reconstruction algorithm (Kinahan 1989; Defrise 1997) and displayed by AMIDE software (Loening 2003). At the last scan time point (168 hours), one representative SCID mouse from each group was also imaged by microCAT™ II tomograph (ImTek Inc., Knoxville, Tenn.) for 10 minutes as described (Chow 2005). The microPET and microCT images were then coregistered to yield a single image. After scanning, tumors, liver and kidneys were excised, weighed and counted in a well counter (Willac Wizard 3", PerkinElmer Life and Analytical Sciences), and after decay correction the % ID/g was calculated. In order to determine positive to negative tumor ratios, regions of interest (ROIs) were drawn as described previously (Sundaresan 2003).

Both antibodies demonstrated specific targeting to the positive tumor and uptake similar to that observed in the biodistribution with $^{111}$In-MX-DTPA mu1G8. At the time of sacrifice (at 94 hours after administration), 13.6 (±4.0) % ID/g of the mu1G8 and 12.7 (±1.6) % ID/g of the hu1G8-B was found in the antigen positive tumor (PC3-PSCA), whereas 9.7 (±2.4) % ID/g of mu1G8 and 7.6 (±2.8) % ID/g of hu1G8-B was found in the antigen negative tumor (C6). Mice bearing LAPC-9 (antigen positive) and PC3 (antigen negative) xenografts were imaged every day for five days, starting at 72 hours and ending at 168 hours after administration (FIG. 6). At 72 hours, most of the activity was seen in the blood pool and normal tissue. This activity disappears by 168 hours. Activity was also seen in the positive tumor at 72 hours, and at 168 hours the highest activity is in the positive tumor as verified by the fused microPET/CT image (far right). The mean positive tumor to background ratios were estimated from the images to be 2.2 at 72 hours and 3.0 at 168 hours for the mu1G8 (n=2), and 1.9 at 72 h and 2.7 at 168 hours for the hu1G8-B (n=3). At the time of sacrifice, 5.8 (±0.8) % ID/g of the mu1G8 and 6.6 (±0.9) % ID/g of the hu1G8-B was found in the antigen positive tumor, whereas 2.6 (±0.5) % ID/g of mu1G8 and 3.3 (±1.1) % ID/g of hu1G8-B was found in the antigen negative tumor (FIGS. 6A and B).

Example 9

Inhibition of Tumor Growth in a Bladder Cancer Model by hu1G8-B

Mice implanted with bladder carcinoma cells were treated with the hu1G8-B. Mice treated with hu1G8-B exhibited markedly lower tumor take and tumor growth than untreated mice or those treated with 1G8. This shows that hu1G8-B is capable of targeting PSCA expressing tumors in vivo, and also possesses significant anti-tumor activity in vivo despite decreased binding affinity compared to 1G8.

SCID mice implanted subcutaneously with $10^6$ SW780 bladder carcinoma cells were treated three times per week with either 1G8 or hu1G8-B antibody at a dosage of 200 µg/mouse via intraperitoneal injection. Control mice received no treatment. A substantial reduction of tumor take was observed in hu1G8-B-treated mice compared to 1G8-treated or untreated mice (FIG. 7). hu1G8-B treatment resulted in approximately a two-fold reduction in tumor take/growth. Thus, despite some loss of binding affinity compared to parental 1G8 antibody, hu1G8-B possesses significant anti-tumor activity in vivo that is actually greater than that of 1G8.

Example 10

Incorporation of Additional Back Mutations into Humanized 1G8

As stated above in Example 4, hu1G8-B was far more active than hu1G8-A with regards to antigen binding activity. This suggests that the C-terminal region of the CDR-H2 loop plays a key role in antigen binding, a conclusion consistent with earlier attempts to humanize an antibody against human protein C (O'Connor 1998). Thus, framework residues that pack against the CDR-H2 loop were scrutinized as potential targets for back mutation.

Prior to proceeding, the molecular model of 1G8 was refined. Although 1QOK remained the most suitable template for modeling 1G8, several new crystal structures with individual CDR loops highly similar or identical to those of 1G8 had been released since the initial model was developed. Comparison of the original model with the new structures suggested that for some residues, non-optimal side chain rotamers had been selected during the modeling procedure. Furthermore, these new crystal structures revealed how several framework residues present in 1G8 influence the conformation of adjacent CDR loops. Based on this, the 1G8 model was rebuilt and 1G8 was re-humanized using the refined model.

Several methods for superimposing the hu4D5v8 crystal structure with the second 1G8 model were evaluated (e.g., superimposing only core packing residues; superimposing only the $V_H$ or $V_L$ frameworks, etc.). Differences between the two Fv units present in the unit cell of the hu4D5v8 crystal structure were compared to see if conformational differences that occur as a result of crystal packing interactions influence in any way the outcome of the 1G8 humanization modeling exercise.

Six additional hu1G8-B residues were selected for back mutation to the corresponding murine residue in an effort to fully restore antigen binding affinity. Six oligonucleotide primers, ranging in length from 34 to 43 oligonucleotides, were used to introduce these back mutations. The sequences of these six primers are set forth in SEQ. ID. NOs:31-36. hu1G8-B residues L70 (aspartic acid, residue 69 in SEQ. ID. NO:7) and L71 (phenylalanine, residue 70 in SEQ. ID. NO:7) pack against the CDR-L1 loop, and in crystal structures with nearly identical CDR-L1 loops these two framework residues influence the conformation of this loop. Based on this, hu1G8-B residues L70 and L71 were replaced with residues L70 and L71 from 1G8 (serine and tyrosine, residues 69 and 70 in SEQ. ID. NO:1). hu1G8-B residues H48 (valine, residue 48 in SEQ. ID. NO:9) and H49 (alanine, residue 49 in SEQ. ID. NO:9), which precede the CDR-H2 loop (H50-H65, residues 50-66 in SEQ. ID. NO:9), were likewise replaced with H48 and H49 from 1G8 (isoleucine and glycine, residues 48 and 49 in SEQ. ID. NO:2). The glycine at residue H49 is particularly important since this residue packs against a hu4D5v8 framework residue (H69) that follows the CDR-H2 loop. Disruption of this pairing causes major shifts of the CDR-H2 loop, either toward or away from the CDR-L3 loop (as seen in the original model of hu1G8-B in which hu4D5v8 residues alanine and isoleucine were retained in these positions). For this reason, residue H69 (isoleucine, residue 70 in SEQ. ID. NO:9) was replaced with residue H69 from 1G8 (methionine, residue 70 in SEQ. ID. NO:2). In addition, hu1G8-B residue H66 (arginine, residue 67 in SEQ. ID. NO:9) was replaced with residue H66 from 1G8 (lysine, residue 67 in SEQ. ID. NO:2) in order to make the post-CDR-H2 framework region essentially identical in 1G8 and the humanized version (residues H67 and H68 are already identical in the murine and humanized sequences). The amino acid sequences of the resultant hu1G8-C light and heavy chains are set forth in SEQ. ID. NOs:37-38, respectively.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Adams, G. P., Weiner, L. M. 2005. Monoclonal antibody therapy of cancer. Nat Biotechnol 23:1147-1157.
2. Bebbington, C., et al. 1992. High-level expression of a recombinant antibody from myeloma cells using a glutamine synthetase gene as an amplifiable selection marker. Biotechnology 10:169-175.
3. Berman, H. M., et al. 2002. The Protein Data Bank. Acta Crystallogr D Biol Crystallogr 58:899-899-907.
4. Boehm, M. K., et al. 2000. Crystal structure of the anti-(carcinoembryonic antigen) single-chain Fv antibody MFE-23 and a model for antigen binding based on intermolecular contacts. Biochem J 346 Pt 2:519-528.
5. Brechbiel, M. W., Gansow, O. A. 1991. Backbone-substituted DTPA ligands for 90Y radioimmunotherapy. Bioconjug Chem 2:187-194.
6. Bruggemann, M., et al. 1991. Human antibody production in transgenic mice: expression from 100 kb of the human IgH locus. Eur J Immunol 5:1323-1326.
7. Chow, P. L., Rannou, F. R., Chatziioannou, A. F. 2005. Attenuation correction for small animal PET tomographs. Phys Med Biol 50:1837-1850.
8. Cobleigh, M. A., et al. 1999. Multinational study of the efficacy and safety of humanized anti-HER2 monoclonal antibody in women who have HER2-overexpressing metastatic breast cancer that has progressed after chemotherapy for metastatic disease. J Clin Oncol 17:2639-2648.
9. Coloma, M. J., et al. 1992. Novel vectors for the expression of antibody molecules using variable regions generated by polymerase chain reaction. J Immunol Methods 152:89-104.
10. Craft, N., et al. 1999. Evidence for clonal outgrowth of androgen-independent prostate cancer cells from androgen-dependent tumors through a two-step process. Cancer Res 59:5030-5036.
11. Defrise, M., et al. 1997. Exact and approximate rebinning algorithms for 3-D PET data. IEEE Trans Med Imaging 16:145-158.
12. Eigenbrot, C., et al. 1993. X-ray structures of the antigen-binding domains from three variants of humanized anti-p185HER2 antibody 4D5 and comparison with molecular modeling. J Mol Biol 229:969-995.
13. Ewert, S., et al. 2003. Biophysical properties of human antibody variable domains. J Mol Biol 325:531-553.
14. Foote, J., Winter, G. 1992. Antibody framework residues affecting the conformation of the hypervariable loops. J Mol Biol 224:487-499.
15. Geissler, F., et al. 1992. Intracellular catabolism of radiolabeled anti-mu antibodies by malignant B-cells. Cancer Res 52:2907-2015.
16. Gu, Z., et al. 2000. Prostate stem cell antigen (PSCA) expression increases with high gleason score, advanced stage and bone metastasis in prostate cancer. Oncogene 19:1288-1296.
17. Gu, Z., et al. 2005. Anti-prostate stem cell antigen monoclonal antibody 1G8 induces cell death in vitro and inhibits tumor growth in vivo via a Fc-independent mechanism. Cancer Res 65:9495-9500.
18. Horton, R. M., et al. 1989. Engineering hybrid genes without the use of restriction enzymes: gene splicing by overlap extension. Gene 77:61-68.
19. Jones, P. T., et al. 1986. Replacing the complementarity-determining regions in a human antibody with those from a mouse. Nature 321:522-525.
20. Kenanova, V., et al. 2005. Tailoring the pharmacokinetics and positron emission tomography imaging properties of anti-carcinoembryonic antigen single-chain Fv-Fc antibody fragments. Cancer Res 65:622-631.
21. Kinahan, P. E., Rogers, J. G. 1989. Analytic 3D image reconstruction using all detected events. IEEE Trans NS 36:964-968.
22. Loening, A. M., Gambhir, S. S. 2003. AMIDE: a free software tool for multimodality medical image analysis. Mol Imaging 2:131-137.
23. Low, N. M., Holliger, P. H., Winter, G. 1996. Mimicking somatic hypermutation: affinity maturation. J Mol Biol 260:359-368.
24. Maynard J., Georgiou, G. 2000. Antibody engineering. Annu Rev Biomed Eng 2:339-376.
25. Mendez, M. J., et al. 1997. Functional transplant of megabase human immunoglobulin loci recapitulates human antibody response in mice. Nat Genet 2:146-156.
26. Nanus, D. M., et al. 2003. Clinical use of monoclonal antibody HuJ591 therapy: targeting prostate specific membrane antigen. J Urol 170:S84-S88; discussion S8-S9.

27. O'Brien, S., Jones, T. 2003. Humanization of monoclonal antibodies by CDR grafting. Methods Mol Biol 207:81-100.
28. O'Connor, S. J., Meng, Y. G., Rezaie, A. R., Presta, L. G. 1998. Humanization of an antibody against human protein C and calcium-dependence involving framework residues. Protein Eng 11:321-328.
29. Olafsen, T., et al. 2004. Characterization of engineered anti-p185HER-2 (scFv-CH3)2 antibody fragments (minibodies) for tumor targeting. Protein Eng Des Sel 17:315-323.
30. Olafsen, T., et al. 2005. Optimizing radiolabeled engineered anti-p185HER2 antibody fragments for in vivo imaging. Cancer Res 65:5907-5916.
31. Pearson, W. R., Lipman, D. J. 1988. Improved tools for biological sequence comparison. Proc Natl Acad Sci USA 85:2444-2448.
32. Reiter, R. E., et al. 1998. Prostate stem cell antigen: a cell surface marker overexpressed in prostate cancer. Proc Natl Acad Sci USA 95:1735-1740.
33. Reiter, R. E., et al. 2000. Coamplification of prostate stem cell antigen (PSCA) and MYC in locally advanced prostate cancer. Genes Chromosomes Cancer 27:95-103.
34. Saffran, D. C., et al. 2001. Anti-PSCA mAbs inhibit tumor growth and metastasis formation and prolong the survival of mice bearing human prostate cancer xenografts. Proc Natl Acad Sci USA 98:2658-2663.
35. Schroff, R. W., Foon, K. A., Beatty, S. M., Oldham, R. K., and Morgan, A. C. Jr. 1985. Human anti-murine responses in patients receiving monoclonal antibody therapy. Cancer Res 45:879-885.
36. Shawler, D. L., Bartholomew, R. M., Smith, L. M., and Dillman, R. O. 1985. Human immune responses to multiple injections of murine monoclonal immunoglobulins. J Immunol 135:1530-1535.
37. Smith-Jones, P. M. 2004. Radioimmunotherapy of prostate cancer. Q J Nucl Med Mol Imaging 48:297-304.
38. Sundaresan, G., et al. 2003. 124I-labeled engineered anti-CEA minibodies and diabodies allow high-contrast, antigen-specific small-animal PET imaging of xenografts in athymic mice. J Nucl Med 44:1962-1969.
39. Winter, G., Griffiths, A. D., Hawkins, R. E., Hoogenboom, H. R. 1994. Making antibodies by phage display technology. Annu Rev Immunol 12:433-455.
40. Worn, A., Pluckthun, A. 1999. Different equilibrium stability behavior of ScFv fragments: identification, classification, and improvement by protein engineering. Biochemistry 38:8739-8750.
41. Wu, A. M., et al. 2001. Multimerization of a chimeric anti-CD20 single-chain Fv-Fc fusion protein is mediated through variable domain exchange. Protein Eng 14:1025-1033.
42. Wu, A. M., Senter, P. D. 2005. Arming antibodies: prospects and challenges for immunoconjugates. Nat Biotechnol 23:1137-1146.
43. Xu, F. J., et al. 1997. Radioiodinated antibody targeting of the HER-2/neu oncoprotein. Nucl Med Biol 24:451-459.
44. Yazaki, P. J., et al. 2001a. Mammalian expression and hollow fiber bioreactor production of recombinant anti-CEA diabody and minibody for clinical applications. J Immunol Methods 253:195-208.
45. Yazaki, P. J., et al. 2001b. Tumor targeting of radiometal labeled anti-CEA recombinant T84.66 diabody and t84.66 minibody: comparison to radioiodinated fragments. Bioconjug Chem 12:220-228.
46. Yazaki, P. J., et al. 2004. Humanization of the anti-CEA T84.66 antibody based on crystal structure data. Protein Eng Des Sel 17:481-489.

What is claimed is:

1. A humanized antibody comprising:
   a) a light chain variable region comprising the amino acid sequence of SEQ ID NO:7 and
   b) a heavy chain variable region comprising the amino acid sequence of SEQ ID NO:9,
   wherein said humanized antibody binds prostate stem cell antigen (PSCA), and wherein administration of said humanized antibody to a subject diagnosed with prostate cancer decreases tumor growth to a greater extent than treatment with the murine 1G8 monoclonal antibody produced by the hybridoma deposited as ATCC No. HB-12612.

2. The humanized antibody of claim 1, wherein said antibody has an affinity constant for prostate stem cell antigen (PSCA) of at least about $2.5 \times 10^8$.

3. The humanized antibody of claim 1, further comprising a conjugate.

4. The humanized antibody of claim 3, wherein said conjugate is selected from the group consisting of a toxin, a cytokine, a chemotherapeutic agent, and a radiolabel.

* * * * *

SEQUENCE LISTING

```
<160> NUMBER OF SEQ ID NOS: 38

<210> SEQ ID NO 1
<211> LENGTH: 106
<212> TYPE: PRT
<213> ORGANISM: Mus musculus
<220> FEATURE:
<221> NAME/KEY: MISC_FEATURE
<222> LOCATION: (24)..(33)
<223> OTHER INFORMATION: CDR-L1 (residues number L24-L34 under Kabat
      system)
<220> FEATURE:
<221> NAME/KEY: MISC_FEATURE
<222> LOCATION: (49)..(55)
<223> OTHER INFORMATION: CDR-L2 (residues number L50-L56 under Kabat
      system)
<220> FEATURE:
<221> NAME/KEY: MISC_FEATURE
<222> LOCATION: (88)..(96)
<223> OTHER INFORMATION: CDR-L3 (residues number L89-L97 under Kabat
      system)

<400> SEQUENCE: 1

Gln Val Val Leu Thr Gln Ser Pro Ala Ile Met Ser Ala Ser Pro Gly
1               5                   10                  15

Glu Lys Val Thr Met Ala Cys Ser Ala Ser Ser Ser Val Arg Phe Ile
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Thr Arg Phe Ser Gly Ser
```

```
                50                  55                  60
Gly Ser Gly Thr Ser Tyr Ser Leu Thr Ile Ser Thr Met Glu Ala Glu
 65                  70                  75                  80

Asp Ala Ala Thr Tyr Tyr Cys Gln Gln Trp Ser Ser Ser Pro Phe Thr
                 85                  90                  95

Phe Gly Ser Gly Thr Lys Leu Ile Ile Lys
                100                 105
```

<210> SEQ ID NO 2
<211> LENGTH: 112
<212> TYPE: PRT
<213> ORGANISM: Mus musculus
<220> FEATURE:
<221> NAME/KEY: MISC_FEATURE
<222> LOCATION: (31)..(35)
<223> OTHER INFORMATION: CDR-H1 (residues number H31-H35 under Kabat system)
<220> FEATURE:
<221> NAME/KEY: MISC_FEATURE
<222> LOCATION: (50)..(66)
<223> OTHER INFORMATION: CDR-H2 (residues number H50-H65 under Kabat system)
<220> FEATURE:
<221> NAME/KEY: MISC_FEATURE
<222> LOCATION: (99)..(101)
<223> OTHER INFORMATION: CDR-H3 (residues number H95-H102 under Kabat system)

<400> SEQUENCE: 2

```
Glu Val Gln Leu Gln Gln Ser Gly Ala Glu Leu Val Arg Ser Gly Ala
 1               5                  10                  15

Ser Val Lys Leu Ser Cys Thr Ala Ser Gly Phe Asn Ile Lys Asp Tyr
                20                  25                  30

Tyr Ile His Trp Val Asn Gln Arg Pro Asp Gln Gly Leu Glu Trp Ile
                35                  40                  45

Gly Trp Ile Asp Pro Glu Asn Gly Asp Thr Glu Phe Val Pro Lys Phe
 50                  55                  60

Gln Gly Lys Ala Thr Met Thr Ala Asp Ile Phe Ser Asn Thr Ala Tyr
 65                  70                  75                  80

Leu His Leu Ser Ser Leu Thr Ser Glu Asp Thr Ala Val Tyr Tyr Cys
                 85                  90                  95

Lys Thr Gly Gly Phe Trp Gly Gln Gly Thr Leu Val Thr Val Ser Ala
                100                 105                 110
```

<210> SEQ ID NO 3
<211> LENGTH: 106
<212> TYPE: PRT
<213> ORGANISM: Mus musculus

<400> SEQUENCE: 3

```
Glu Asn Val Leu Thr Gln Ser Pro Ala Ile Met Ser Ala Ser Pro Gly
 1               5                  10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
                35                  40                  45

Ser Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Leu Thr
                 85                  90                  95
```

```
Phe Gly Ala Gly Thr Lys Leu Glu Leu Lys
            100                 105

<210> SEQ ID NO 4
<211> LENGTH: 120
<212> TYPE: PRT
<213> ORGANISM: Mus musculus

<400> SEQUENCE: 4

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser
        115                 120

<210> SEQ ID NO 5
<211> LENGTH: 107
<212> TYPE: PRT
<213> ORGANISM: Artificial
<220> FEATURE:
<223> OTHER INFORMATION: Variable light chain of humanized anti-p185HER2
      antibody 4D5, version 8
<220> FEATURE:
<221> NAME/KEY: MISC_FEATURE
<222> LOCATION: (24)..(34)
<223> OTHER INFORMATION: CDR-L1 (residues number L24-L34 under Kabat
      system)
<220> FEATURE:
<221> NAME/KEY: MISC_FEATURE
<222> LOCATION: (50)..(56)
<223> OTHER INFORMATION: CDR-L2 (residues number L50-L56 under Kabat
      system)
<220> FEATURE:
<221> NAME/KEY: MISC_FEATURE
<222> LOCATION: (89)..(97)
<223> OTHER INFORMATION: CDR-L3 (residues number L89-L97 under Kabat
      system)

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys
            100                 105
```

<210> SEQ ID NO 6
<211> LENGTH: 120
<212> TYPE: PRT
<213> ORGANISM: Artificial
<220> FEATURE:
<223> OTHER INFORMATION: Variable heavy chain of humanized anti-p185HER2
      antibody 4D5, version 8
<220> FEATURE:
<221> NAME/KEY: MISC_FEATURE
<222> LOCATION: (31)..(35)
<223> OTHER INFORMATION: CDR-H1 (residues number H31-H35 under Kabat
      system)
<220> FEATURE:
<221> NAME/KEY: MISC_FEATURE
<222> LOCATION: (50)..(66)
<223> OTHER INFORMATION: CDR-H2 (residues number H50-H65 under Kabat
      system)
<220> FEATURE:
<221> NAME/KEY: MISC_FEATURE
<222> LOCATION: (99)..(109)
<223> OTHER INFORMATION: CDR-H3 (residues number H95-H102 under Kabat
      system)

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 7
<211> LENGTH: 106
<212> TYPE: PRT
<213> ORGANISM: Artificial
<220> FEATURE:
<223> OTHER INFORMATION: Artificially constructed variable light chain
      of hu1G8-A and hu1G8-B
<220> FEATURE:
<221> NAME/KEY: MISC_FEATURE
<222> LOCATION: (4)..()
<223> OTHER INFORMATION: Murine back mutation (residue number L4 under
      Kabat system)
<220> FEATURE:
<221> NAME/KEY: MISC_FEATURE
<222> LOCATION: (24)..(33)
<223> OTHER INFORMATION: CDR-L1 (residues number L24-L34 under Kabat
      system)
<220> FEATURE:
<221> NAME/KEY: MISC_FEATURE
<222> LOCATION: (24)..(33)
<223> OTHER INFORMATION: Murine residues (residues number L24-L34 under
      Kabat system)
<220> FEATURE:
<221> NAME/KEY: MISC_FEATURE
<222> LOCATION: (45)..()
<223> OTHER INFORMATION: Murine back mutation (residue number L46 under

```
                                   Kabat system)
<220> FEATURE:
<221> NAME/KEY: MISC_FEATURE
<222> LOCATION: (49)..(55)
<223> OTHER INFORMATION: CDR-L2 (residues number L50-L56 under Kabat
      system)
<220> FEATURE:
<221> NAME/KEY: MISC_FEATURE
<222> LOCATION: (49)..(55)
<223> OTHER INFORMATION: Murine residues (residues number L50-L56 under
      Kabat system)
<220> FEATURE:
<221> NAME/KEY: MISC_FEATURE
<222> LOCATION: (65)..()
<223> OTHER INFORMATION: Murine back mutation (residue number L66 under
      Kabat system)
<220> FEATURE:
<221> NAME/KEY: MISC_FEATURE
<222> LOCATION: (88)..(96)
<223> OTHER INFORMATION: CDR-L3 (residues number L89-L97 under Kabat
      system)
<220> FEATURE:
<221> NAME/KEY: MISC_FEATURE
<222> LOCATION: (88)..(96)
<223> OTHER INFORMATION: Murine residues (residues number L89-L97 under
      Kabat system)

<400> SEQUENCE: 7

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys
            100                 105

<210> SEQ ID NO 8
<211> LENGTH: 112
<212> TYPE: PRT
<213> ORGANISM: Artificial
<220> FEATURE:
<223> OTHER INFORMATION: Artificially constructed variable heavy chain
      of hu1G8-A
<220> FEATURE:
<221> NAME/KEY: MISC_FEATURE
<222> LOCATION: (26)..(35)
<223> OTHER INFORMATION: Murine residues (residues number H26-H35 under
      Kabat system)
<220> FEATURE:
<221> NAME/KEY: MISC_FEATURE
<222> LOCATION: (31)..(35)
<223> OTHER INFORMATION: CDR-H1 (residues number H31-H35 under Kabat
      system)
<220> FEATURE:
<221> NAME/KEY: MISC_FEATURE
<222> LOCATION: (50)..(60)
<223> OTHER INFORMATION: Murine residues (residues number H50-H59 under
      Kabat system)
<220> FEATURE:
<221> NAME/KEY: MISC_FEATURE
<222> LOCATION: (50)..(66)
<223> OTHER INFORMATION: CDR-H2 (residues number H50-H65 under Kabat
      system)
<220> FEATURE:
<221> NAME/KEY: MISC_FEATURE
```

```
<222> LOCATION: (97)..(101)
<223> OTHER INFORMATION: Murine residues (residues number H93-H102 under
      Kabat system)
<220> FEATURE:
<221> NAME/KEY: MISC_FEATURE
<222> LOCATION: (99)..(101)
<223> OTHER INFORMATION: CDR-H3 (residues number H95-H102 under Kabat
      system)

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Val
        35                  40                  45

Ala Trp Ile Asp Pro Glu Asn Gly Asp Thr Glu Phe Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110

<210> SEQ ID NO 9
<211> LENGTH: 112
<212> TYPE: PRT
<213> ORGANISM: Artificial
<220> FEATURE:
<223> OTHER INFORMATION: Artificially constructed variable heavy chain
      of hu1G8-B
<220> FEATURE:
<221> NAME/KEY: MISC_FEATURE
<222> LOCATION: (26)..(35)
<223> OTHER INFORMATION: Murine residues (residues number H26-H35 under
      Kabat system)
<220> FEATURE:
<221> NAME/KEY: MISC_FEATURE
<222> LOCATION: (31)..(35)
<223> OTHER INFORMATION: CDR-H1 (residues number H31-H35 under Kabat
      system)
<220> FEATURE:
<221> NAME/KEY: MISC_FEATURE
<222> LOCATION: (50)..(66)
<223> OTHER INFORMATION: CDR-H2 (residues number H50-H65 under Kabat
      system)
<220> FEATURE:
<221> NAME/KEY: MISC_FEATURE
<222> LOCATION: (50)..(66)
<223> OTHER INFORMATION: Murine residues (residues number H50-H65 under
      Kabat system)
<220> FEATURE:
<221> NAME/KEY: MISC_FEATURE
<222> LOCATION: (68)..()
<223> OTHER INFORMATION: Murine back mutation (residue number H67 under
      Kabat system)
<220> FEATURE:
<221> NAME/KEY: MISC_FEATURE
<222> LOCATION: (97)..(101)
<223> OTHER INFORMATION: Murine residues (residues number H93-H102 under
      Kabat system)
<220> FEATURE:
<221> NAME/KEY: MISC_FEATURE
<222> LOCATION: (99)..(101)
<223> OTHER INFORMATION: CDR-H3 (residues number H95-H102 under Kabat
      system)

<400> SEQUENCE: 9

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Val
        35                  40                  45

Ala Trp Ile Asp Pro Glu Asn Gly Asp Thr Glu Phe Val Pro Lys Phe
    50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110

<210> SEQ ID NO 10
<211> LENGTH: 78
<212> TYPE: DNA
<213> ORGANISM: Artificial
<220> FEATURE:
<223> OTHER INFORMATION: Synthetic oligonucleotide

<400> SEQUENCE: 10
tcgatcgact ctagagccgc caccatggag acagacacac tcctgctatg ggtgctgctg        60
ctctgggttc caggttcc                                                     78

<210> SEQ ID NO 11
<211> LENGTH: 79
<212> TYPE: DNA
<213> ORGANISM: Artificial
<220> FEATURE:
<223> OTHER INFORMATION: Synthetic oligonucleotide

<400> SEQUENCE: 11
tgggtgctgc tgctctgggt tccaggttcc acaggtgaca ttcagctgac ccaatctcca        60
agctctttgt ccgcctctg                                                    79

<210> SEQ ID NO 12
<211> LENGTH: 79
<212> TYPE: DNA
<213> ORGANISM: Artificial
<220> FEATURE:
<223> OTHER INFORMATION: Synthetic oligonucleotide

<400> SEQUENCE: 12
cccaatctcc aagctctttg tccgcctctg tgggggatag ggtcaccatc acctgcagtg        60
ccagttcaag tgtaagatt                                                    79

<210> SEQ ID NO 13
<211> LENGTH: 64
<212> TYPE: DNA
<213> ORGANISM: Artificial
<220> FEATURE:
<223> OTHER INFORMATION: Synthetic oligonucleotide

<400> SEQUENCE: 13
cacctgcagt gccagttcaa gtgtaagatt cattcactgg taccagcaga aaccaggaaa        60
agct                                                                    64

<210> SEQ ID NO 14
<211> LENGTH: 79
<212> TYPE: DNA
<213> ORGANISM: Artificial

```
<220> FEATURE:
<223> OTHER INFORMATION: Synthetic oligonucleotide

<400> SEQUENCE: 14
aagggacgcc agaagccagt ttggatgtgt catagatgag tcttttggga gcttttcctg    60
gtttctgctg gtaccagtg                                                 79

<210> SEQ ID NO 15
<211> LENGTH: 79
<212> TYPE: DNA
<213> ORGANISM: Artificial
<220> FEATURE:
<223> OTHER INFORMATION: Synthetic oligonucleotide

<400> SEQUENCE: 15
ctaatggtga gggtgaagtc tgtcccagac ccggagccac tgaacctaga agggacgcca    60
gaagccagtt tggatgtgt                                                 79

<210> SEQ ID NO 16
<211> LENGTH: 79
<212> TYPE: DNA
<213> ORGANISM: Artificial
<220> FEATURE:
<223> OTHER INFORMATION: Synthetic oligonucleotide

<400> SEQUENCE: 16
actccactgc tgacagtaat aggtggcgaa atcttccggc tgcagactgc taatggtgag    60
ggtgaagtct gtcccagac                                                 79

<210> SEQ ID NO 17
<211> LENGTH: 78
<212> TYPE: DNA
<213> ORGANISM: Artificial
<220> FEATURE:
<223> OTHER INFORMATION: Synthetic oligonucleotide

<400> SEQUENCE: 17
acgttttatc tcgagcttgg tcccctgtcc gaacgtgaat gggctactac tccactgctg    60
acagtaatag gtggcgaa                                                  78

<210> SEQ ID NO 18
<211> LENGTH: 88
<212> TYPE: DNA
<213> ORGANISM: Artificial
<220> FEATURE:
<223> OTHER INFORMATION: Synthetic oligonucleotide

<400> SEQUENCE: 18
tcgatcgact ctagagccgc caccatgaaa tgcagctggg ttatcttctt cctgatggca    60
gtggttacag gggtcaattc agaggttc                                       88

<210> SEQ ID NO 19
<211> LENGTH: 89
<212> TYPE: DNA
<213> ORGANISM: Artificial
<220> FEATURE:
<223> OTHER INFORMATION: Synthetic oligonucleotide

<400> SEQUENCE: 19
cagtggttac agggtcaat tcagaggttc agctggtgga gtctggggt ggccttgtgc     60 agccaggggg ctcactccgt ttgtcctgc                                      89
```

```
<210> SEQ ID NO 20
<211> LENGTH: 88
<212> TYPE: DNA
<213> ORGANISM: Artificial
<220> FEATURE:
<223> OTHER INFORMATION: Synthetic oligonucleotide

<400> SEQUENCE: 20
cagccagggg gctcactccg tttgtcctgc gcagcttctg gcttcaacat taaagactac    60
tatatacact gggtgcgtca ggcccctg                                       88

<210> SEQ ID NO 21
<211> LENGTH: 87
<212> TYPE: DNA
<213> ORGANISM: Artificial
<220> FEATURE:
<223> OTHER INFORMATION: Synthetic oligonucleotide

<400> SEQUENCE: 21
actatataca ctgggtgcgt caggcccctg gtaagggcct ggaatgggtt gcatggattg    60
atcctgagaa tggtgacact gaatttg                                        87

<210> SEQ ID NO 22
<211> LENGTH: 89
<212> TYPE: DNA
<213> ORGANISM: Artificial
<220> FEATURE:
<223> OTHER INFORMATION: Synthetic oligonucleotide

<400> SEQUENCE: 22
aggtaggctg tgttttgga tgtgtctgcg cttatagtgg cacggccctg gaacttcggg     60
acaaattcag tgtcaccatt ctcaggatc                                      89

<210> SEQ ID NO 23
<211> LENGTH: 88
<212> TYPE: DNA
<213> ORGANISM: Artificial
<220> FEATURE:
<223> OTHER INFORMATION: Synthetic oligonucleotide

<400> SEQUENCE: 23 acccccccgtt ttacaataat agacggcagt gtcctcagca cgcaggctgt tcatctgcag   60
gtaggctgtg ttttggatg tgtctgcg                                        88

<210> SEQ ID NO 24
<211> LENGTH: 62
<212> TYPE: DNA
<213> ORGANISM: Artificial
<220> FEATURE:
<223> OTHER INFORMATION: Synthetic oligonucleotide

<400> SEQUENCE: 24
gagacggtga ccaggggttcc ttgaccccag aaaccccccg ttttacaata atagacggca   60
gt                                                                   62

<210> SEQ ID NO 25
<211> LENGTH: 88
<212> TYPE: DNA
<213> ORGANISM: Artificial
<220> FEATURE:
<223> OTHER INFORMATION: Synthetic oligonucleotide

<400> SEQUENCE: 25
ggtgctcttg ctcgagggtg ccaggggggaa gaccgatggg cccttagtgg aggctgagga   60
```

```
gacggtgacc agggttcctt gaccccag                                        88

<210> SEQ ID NO 26
<211> LENGTH: 405
<212> TYPE: DNA
<213> ORGANISM: Artificial
<220> FEATURE:
<223> OTHER INFORMATION: hu1G8-A/hu1G8-B VL chain PCR product

<400> SEQUENCE: 26
tcgatcgact ctagagccgc caccatggag acagacacac tcctgctatg ggtgctgctg    60
ctctgggttc caggttccac aggtgacatt cagctgaccc aatctccaag ctctttgtcc   120
gcctctgtgg gggatagggt caccatcacc tgcagtgcca gttcaagtgt aagattcatt   180
cactggtacc agcagaaacc aggaaaagct cccaaaagac tcatctatga cacatccaaa   240
ctggcttctg gcgtcccttc taggttcagt ggctccgggt ctgggacaga cttcaccctc   300
accattagca gtctgcagcc ggaagatttc gccacctatt actgtcagca gtggagtagt   360
agcccattca cgttcggaca ggggaccaag gtggagataa aacgt                   405

<210> SEQ ID NO 27
<211> LENGTH: 471
<212> TYPE: DNA
<213> ORGANISM: Artificial
<220> FEATURE:
<223> OTHER INFORMATION: hu1G8-A VH chain PCR product

<400> SEQUENCE: 27
tcgatcgact ctagagccgc caccatgaaa tgcagctggg ttatcttctt cctgatggca    60
gtggttacag gggtcaattc agaggttcag ctggtggagt ctgggggtgg ccttgtgcag   120 ccaggggggct cactccgttt gtcctgcgca gcttctggct tcaacattaa agactactat   180
atacactggg tgcgtcaggc ccctggtaag ggcctggaat gggttgcatg gattgatcct   240
gagaatggtg acactgaatt tgccgatagc gtcaagggcc gtttcactat aagcgcagac   300
acatccaaaa acacagccta cctgcagatg aacagcctgc gtgctgagga cactgccgtc   360
tattattgta aaacgggggg tttctggggt caaggaaccc tggtcaccgt ctcctcagcc   420
tccactaagg gcccatcggt cttccccctg gcaccctcga gcaagagcac c            471

<210> SEQ ID NO 28
<211> LENGTH: 471
<212> TYPE: DNA
<213> ORGANISM: Artificial
<220> FEATURE:
<223> OTHER INFORMATION: hu1G8-B VH chain PCR product

<400> SEQUENCE: 28
tcgatcgact ctagagccgc caccatgaaa tgcagctggg ttatcttctt cctgatggca    60
gtggttacag gggtcaattc agaggttcag ctggtggagt ctgggggtgg ccttgtgcag   120 ccaggggggct cactccgttt gtcctgcgca gcttctggct tcaacattaa agactactat   180
atacactggg tgcgtcaggc ccctggtaag ggcctggaat gggttgcatg gattgatcct   240
gagaatggtg acactgaatt tgtcccgaag ttccagggcc gtgccactat aagcgcagac   300
acatccaaaa acacagccta cctgcagatg aacagcctgc gtgctgagga cactgccgtc   360
tattattgta aaacgggggg tttctggggt caaggaaccc tggtcaccgt ctcctcagcc   420
tccactaagg gcccatcggt cttccccctg gcaccctcga gcaagagcac c            471
```

```
<210> SEQ ID NO 29
<211> LENGTH: 318
<212> TYPE: DNA
<213> ORGANISM: Artificial
<220> FEATURE:
<223> OTHER INFORMATION: Artificially constructed coding sequence for
      variable light chain of hu1G8-B

<400> SEQUENCE: 29
gacattcagc tgacccaatc tccaagctct ttgtccgcct ctgtggggga tagggtcacc     60
atcacctgca gtgccagttc aagtgtaaga ttcattcact ggtaccagca gaaaccagga   120
aaagctccca aaagactcat ctatgacaca tccaaactgg cttctggcgt cccttctagg   180
ttcagtggct ccgggtctgg gacagacttc accctcacca ttagcagtct gcagccggaa   240
gatttcgcca cctattactg tcagcagtgg agtagtagcc cattcacgtt cggacagggg   300
accaaggtgg agataaaa                                                 318

<210> SEQ ID NO 30
<211> LENGTH: 336
<212> TYPE: DNA
<213> ORGANISM: Artificial
<220> FEATURE:
<223> OTHER INFORMATION: Artificially constructed coding sequence for
      variable heavy chain of hu1G8-B

<400> SEQUENCE: 30
gaggttcagc tggtggagtc tgggggtggc ttgtgcagc caggggggctc actccgtttg    60 tcctgcgcag cttctggctt caacattaaa gactactata tacactgggt gcgtcaggcc   120
cctggtaagg gcctggaatg ggttgcatgg attgatcctg agaatggtga cactgaattt   180
gtcccgaagt tccagggccg tgccactata agcgcagaca catccaaaaa cacagcctac   240
ctgcagatga acagcctgcg tgctgaggac actgccgtct attattgtaa aacggggggt   300
ttctggggtc aaggaaccct ggtcaccgtc tcctca                             336

<210> SEQ ID NO 31
<211> LENGTH: 40
<212> TYPE: DNA
<213> ORGANISM: Artificial
<220> FEATURE:
<223> OTHER INFORMATION: Synthetic oligonucleotide

<400> SEQUENCE: 31
gctccgggtc tgggacatct tacaccctca ccattagcag                          40

<210> SEQ ID NO 32
<211> LENGTH: 40
<212> TYPE: DNA
<213> ORGANISM: Artificial
<220> FEATURE:
<223> OTHER INFORMATION: Synthetic oligonucleotide

<400> SEQUENCE: 32
ctgctaatgg tgagggtgta agatgtccca gacccggagc                          40

<210> SEQ ID NO 33
<211> LENGTH: 34
<212> TYPE: DNA
<213> ORGANISM: Artificial
<220> FEATURE:
<223> OTHER INFORMATION: Synthetic oligonucleotide

<400> SEQUENCE: 33
gggcctggaa tggattggat ggattgatcc tgag                                34
```

```
<210> SEQ ID NO 34
<211> LENGTH: 34
<212> TYPE: DNA
<213> ORGANISM: Artificial
<220> FEATURE:
<223> OTHER INFORMATION: Synthetic oligonucleotide

<400> SEQUENCE: 34
ctcaggatca atccatccaa tccattccag gccc                                   34

<210> SEQ ID NO 35
<211> LENGTH: 43
<212> TYPE: DNA
<213> ORGANISM: Artificial
<220> FEATURE:
<223> OTHER INFORMATION: Synthetic oligonucleotide

<400> SEQUENCE: 35
cccgaagttc cagggcaagg ccactatgag cgcagacaca tcc                         43

<210> SEQ ID NO 36
<211> LENGTH: 43
<212> TYPE: DNA
<213> ORGANISM: Artificial
<220> FEATURE:
<223> OTHER INFORMATION: Synthetic oligonucleotide

<400> SEQUENCE: 36
ggatgtgtct gcgctcatag tggccttgcc ctggaacttc ggg                         43

<210> SEQ ID NO 37
<211> LENGTH: 106
<212> TYPE: PRT
<213> ORGANISM: Artificial
<220> FEATURE:
<223> OTHER INFORMATION: Artificially constructed variable light chain
      of hu1G8-C
<220> FEATURE:
<221> NAME/KEY: MISC_FEATURE
<222> LOCATION: (4)..()
<223> OTHER INFORMATION: Murine back mutation (residue number L4 under
      Kabat system)
<220> FEATURE:
<221> NAME/KEY: MISC_FEATURE
<222> LOCATION: (24)..(33)
<223> OTHER INFORMATION: CDR-L1 (residues number L24-L34 under Kabat
      system)
<220> FEATURE:
<221> NAME/KEY: MISC_FEATURE
<222> LOCATION: (24)..(33)
<223> OTHER INFORMATION: Murine residues (residues number L24-L34 under
      Kabat system)
<220> FEATURE:
<221> NAME/KEY: MISC_FEATURE
<222> LOCATION: (45)..()
<223> OTHER INFORMATION: Murine back mutation (residue number L46 under
      Kabat system)
<220> FEATURE:
<221> NAME/KEY: MISC_FEATURE
<222> LOCATION: (49)..(55)
<223> OTHER INFORMATION: CDR-L2 (residues number L50-L56 under Kabat
      system)
<220> FEATURE:
<221> NAME/KEY: MISC_FEATURE
<222> LOCATION: (49)..(55)
<223> OTHER INFORMATION: Murine residues (residues number L50-L56 under
      Kabat system)
<220> FEATURE:
<221> NAME/KEY: MISC_FEATURE
<222> LOCATION: (65)..()
<223> OTHER INFORMATION: Murine back mutation (residue number L66 under
      Kabat system)
```

<220> FEATURE:
<221> NAME/KEY: MISC_FEATURE
<222> LOCATION: (69)..()
<223> OTHER INFORMATION: Murine back mutation (residue number L70 under
      Kabat system)
<220> FEATURE:
<221> NAME/KEY: MISC_FEATURE
<222> LOCATION: (70)..()
<223> OTHER INFORMATION: Murine back mutation (residue number L71 under
      Kabat system)
<220> FEATURE:
<221> NAME/KEY: MISC_FEATURE
<222> LOCATION: (88)..(96)
<223> OTHER INFORMATION: CDR-L3 (residues number L89-L97 under Kabat
      system)
<220> FEATURE:
<221> NAME/KEY: MISC_FEATURE
<222> LOCATION: (88)..(96)
<223> OTHER INFORMATION: Murine residues (residues number L89-L97 under
      Kabat system)

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys
            100                 105

<210> SEQ ID NO 38
<211> LENGTH: 112
<212> TYPE: PRT
<213> ORGANISM: Artificial
<220> FEATURE:
<223> OTHER INFORMATION: Artificially constructed variable heavy chain
      of hu1G8-C
<220> FEATURE:
<221> NAME/KEY: MISC_FEATURE
<222> LOCATION: (26)..(35)
<223> OTHER INFORMATION: Murine residues (residue number H26-H35 under
      Kabat system)
<220> FEATURE:
<221> NAME/KEY: MISC_FEATURE
<222> LOCATION: (31)..(35)
<223> OTHER INFORMATION: CDR-H1 (residue number H31-H35 under Kabat
      system)
<220> FEATURE:
<221> NAME/KEY: MISC_FEATURE
<222> LOCATION: (48)..()
<223> OTHER INFORMATION: Murine back mutation (residue number H48 under
      Kabat system)
<220> FEATURE:
<221> NAME/KEY: MISC_FEATURE
<222> LOCATION: (49)..()
<223> OTHER INFORMATION: Murine back mutation (residue number H49 under
      Kabat system)
<220> FEATURE:
<221> NAME/KEY: MISC_FEATURE
<222> LOCATION: (50)..(66)
<223> OTHER INFORMATION: CDR-H2 (residue number H50-H65 under Kabat
      system)
<220> FEATURE:
<221> NAME/KEY: MISC_FEATURE
<222> LOCATION: (50)..(66)

```
<223> OTHER INFORMATION: Murine residues (residue number H50-H65 under
      Kabat system)
<220> FEATURE:
<221> NAME/KEY: MISC_FEATURE
<222> LOCATION: (67)..()
<223> OTHER INFORMATION: Murine back mutation (residue number H66 under
      Kabat system)
<220> FEATURE:
<221> NAME/KEY: MISC_FEATURE
<222> LOCATION: (68)..()
<223> OTHER INFORMATION: Murine back mutation (residue number H67 under
      Kabat system)
<220> FEATURE:
<221> NAME/KEY: MISC_FEATURE
<222> LOCATION: (70)..()
<223> OTHER INFORMATION: Murine back mutation (residue number H69 under
      Kabat system)
<220> FEATURE:
<221> NAME/KEY: MISC_FEATURE
<222> LOCATION: (97)..(101)
<223> OTHER INFORMATION: Murine residues (residue number H93-H102 under
      Kabat system)
<220> FEATURE:
<221> NAME/KEY: MISC_FEATURE
<222> LOCATION: (99)..(101)
<223> OTHER INFORMATION: CDR-H3 (residue number H95-H102 under Kabat
      system)

<400> SEQUENCE: 38

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Ile
        35                  40                  45

Gly Trp Ile Asp Pro Glu Asn Gly Asp Thr Glu Phe Val Pro Lys Phe
    50                  55                  60

Gln Gly Lys Ala Thr Met Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110
```